US008263403B2

(12) United States Patent
Perry et al.

(10) Patent No.: US 8,263,403 B2
(45) Date of Patent: Sep. 11, 2012

(54) METHODS AND COMPOSITIONS FOR STEM CELL SELF-RENEWAL

(75) Inventors: John M. Perry, Olathe, KS (US);
Linheng Li, Kansas City, MO (US);
Justin C. Grindley, Kansas City, MO (US)

(73) Assignee: Stowers Institute for Medical Research, Kansas City, MO (US)

( * ) Notice: Subject to any disclaimer, the term of this patent is extended or adjusted under 35 U.S.C. 154(b) by 141 days.

(21) Appl. No.: 12/451,038

(22) PCT Filed: Apr. 23, 2008

(86) PCT No.: PCT/US2008/005230
§ 371 (c)(1),
(2), (4) Date: Apr. 5, 2010

(87) PCT Pub. No.: WO2008/133904
PCT Pub. Date: Nov. 6, 2008

(65) Prior Publication Data
US 2010/0196337 A1 Aug. 5, 2010

Related U.S. Application Data

(60) Provisional application No. 60/926,065, filed on Apr. 23, 2007, provisional application No. 61/066,693, filed on Feb. 22, 2008.

(51) Int. Cl.
*C12N 5/00* (2006.01)
*C12N 5/02* (2006.01)
*C12N 5/071* (2010.01)
*C12N 5/07* (2010.01)
*C12N 5/10* (2006.01)

(52) U.S. Cl. ........ 435/377; 435/375; 435/372; 435/355; 435/325

(58) Field of Classification Search .................. 435/377
See application file for complete search history.

(56) References Cited

U.S. PATENT DOCUMENTS

| | | | |
|---|---|---|---|
| 5,958,769 | A | 9/1999 | Roberts et al. |
| 7,169,605 | B2 | 1/2007 | Peled et al. |
| 7,955,852 | B2 | 6/2011 | Peled et al. |
| 8,080,417 | B2 | 12/2011 | Peled et al. |
| 2005/0158857 | A1 | 7/2005 | Yilmaz et al. |
| 2006/0147435 | A1 | 7/2006 | Moon et al. |
| 2006/0275823 | A1 | 12/2006 | Kodadek |
| 2007/0065447 | A1 | 3/2007 | Tryggvason et al. |
| 2009/0093026 | A1 | 4/2009 | Dowdy et al. |
| 2009/0285786 | A1 | 11/2009 | Zon et al. |
| 2010/0099186 | A1 | 4/2010 | Perry et al. |

FOREIGN PATENT DOCUMENTS

| | | |
|---|---|---|
| WO | WO 90/10448 | 9/1990 |
| WO | WO 91/04753 | 4/1991 |
| WO | WO 2004/048536 | 6/2004 |
| WO | WO 2006/027545 | 3/2006 |

OTHER PUBLICATIONS

Patil, The AAPS Journal, 7(1): Article 9, E61-E77, 2005.*
Akashi et al., "A Clonogenic Common Myeloid Progenitor That Gives Rise to All Myeloid Lineages," Nature, 404, pp. 193-197 (2000).
Antonchuk et al., "HOXB4-Induced Expansion of Adult Hematopoietic Stem Cells Ex Vivo," Cell, 109, pp. 39-45 (2002).
Arai et al., "Tie2/Angiopoietin-1 Signaling Regulates Hematopoietic Stem Cell Quiescence in the Bone Marrow Niche," Cell, 118, pp. 149-161 (2004).
Burgering et al., "Decisions on Life and Death: FOXO Forkhead Transcription Factors Are in Command When PKB/Akt is Off Duty," Journal of Leukocyte Biology, 73, pp. 689-701 (2003).
Calvi et al., "Osteoblastic Cells Regulate the Haematopoietic Stem Cell Niche," Nature, 425, pp. 841-846 (2003).
Caplen et al., "Specific Inhibition of Gene Expression by Small Double-Stranded RNAs in Invertebrate and Vertebrate Systems," PNAS, 98(17), pp. 9742-9747 (2001).
Cardone et al., "Regulation of Cell Death Protease Caspase-9 by Phosphorylation," Science, 282(5392), pp. 1318-1321 (1998).
Casset et al., "A Peptide Mimetic of an Anti-CD4 Monoclonal Antibody by Rational Design," Biochem. Biophys. Res. Commun., 307(1), pp. 198-205 (2003).
Christensen et al., "Flk-2 Is a Marker in Hematopoietic Stem Cell Differentiation: A Simple Method to Isolate Long-Term Stem Cells," PNAS, 98(25), pp. 14541-14546 (2001).
Cobas et al., "Beta-Catenin Is Dispensable for Hematopoiesis and Lymphopiesis," J. Exp. Med., 199(2), pp. 221-229 (2004).
Cortez-Retamozo et al., "Efficient Cancer Therapy With a Nanobody-Based Conjugate," Cancer Research, 64, pp. 2853-2857 (2004).
Cross et al., "Inhibition of Glycogen Synthase Kinase-3 by Insulin Mediated by Protein Kinase B," Nature, 378, pp. 785-789 (1995).
Cui et al., "Muscarinic Acetylcholine Receptors Mediate Oligodendrocyte Progenitor Survival Through Src-like Tyrosine Kinases and PI3K/Akt Pathways," Neurochem. Int., 48(5), pp. 383-393 (2006).
Cully et al., "Beyond PTEN Mutations: the PI3K Pathway as an Integrator of Multiple Inputs During Tumorigenesis," Nature Review Cancer, 6, pp. 184-192 (2006).
Datta et al., "Akt Phosphorylation of BAD Couples Survival Signals to the Cell-Intrinsic Death Machinery," Cell, 91, pp. 231-241 (1997).
Datta et al., "Cellular Survival: A Play in Three Akts," Genes & Development, 13, 2905-2927 (1999).
Donepudi et al., "Structure and Zymogen Activation of Caspases," Biophys. Chem., vols. 101-102, pp. 145-153 (2002).
Elbashir et al., "Duplexes of 21-Nucleotide RNAs Mediate RNA Interference in Cultured Mammalian Cells," Nature, 411, pp. 494-498 (2001).
El-Deiry et al., "WAF1, a Potential Mediator of P53 Tumor Suppression," Cell, 75(4), pp. 817-825 (1993).

(Continued)

*Primary Examiner* — Valarie Bertoglio
(74) *Attorney, Agent, or Firm* — Bryan Cave LLP

(57) ABSTRACT

The present invention relates to methods for expanding a stem cell population. More particularly, the invention relates, inter alia, to methods and compositions for expanding a stem cell population, particularly a hematopoietic stem cell population.

30 Claims, 25 Drawing Sheets

OTHER PUBLICATIONS

Fassina, "Complementary Peptides as Antibody Mimetics for Protein Purification and Assay," Immunomethods, 5(2), pp. 121-129 (1994).
Foster, "Regulation of mTOR by Phosphatidic Acid?," Cancer Res., 67 (1), pp. 1-4 (2007).
Fujita et al., "Akt-Dependent Phosphorylation of p27Kip1 Promotes Binding to 14-3-3 and Cytoplasmic Localization," J. Biol. Chem., 277(32), pp. 28706-28713 (2002).
Gilley et al., "FOXO Transcription Factors Directly Activate Bim Gene Expression and Promote Apoptosis in Sympathetic Neurons," J. Cell Biol., 162(4), pp. 613-622 (2003).
Goessling et al., "Genetic Interaction of PGE2 and Wnt Signaling Regulates Developmental Specification of Stem Cells and Regeneration," Cell, 136, pp. 1136-1147 (2009).
Göthert et al., In Vivo Fate-Tracing Studies Using the Scl Stem Cell Enhancer: Embryonic Hematopoietic Stem Cells Significantly Contribute to Adult Hematopoiesis, Blood Journal, 105(7), pp. 2724-2732 (2005).
Gottlieb et al., "Cross-talk Between Akt, p53 and Mdm2: Possible Implications for the Regulation of Apoptosis," Oncogene, 21(8), pp. 1299-1303 (2002).
Gray et al., "Trichofolliculoma," Arch. Dermatol., 86(5), pp. 619-625 (1962).
Guo et al., "Multi-Genetic Events Collaboratively Contribute to Pten-null Leukaemia Stem-Cell Formation," Nature, 453, pp. 529-533 (2008).
Hagen et al., "Expression and Characterization of GSK-3 Mutants and Their Effect on β-Catenin Phosphorylation in Intact Cells," J. Biol. Chem., 277(26), pp. 23330-23335 (2002).
Harada et al., "Intestinal Polyposis in Mice With a Dominant Stable Mutation of the β-Catenin Gene," EMBO Journal, 18(21), pp. 5931-5942 (1999).
Harborth et al., "Identification of Essential Genes in Cultured Mammalian Cells Using Small Interfering RNAs," Journal of Cell Science, 114(24), pp. 4557-4565 (2001).
Haupt et al., "Mdm2 Promotes the Rapid Degradation of P53," Nature, 387, pp. 296-299 (1997).
He et al., "PTEN-Deficient Intestinal Stem Cells Initiate Intestinal Polyposis," Nature Genetics, 39(2), pp. 189-198 (2007).
Heissig et al., "Recruitment of Stem and Progenitor Cells From the Bone Marrow Niche Requires MMP-9 Mediated Release of Kit-Ligand," Cell, 109, pp. 625-637 (2002).
Hsu et al., "Interference of BAD (Bcl-xL/Bcl-2-Associated Death Promoter)-Induced Apoptosis in Mammalian Cells by 14-3-3 Isoforms and P11," Molecular Endocrinology, 11(12), pp. 1858-1867 (1997).
Hui et al., "The Neuroprotection of Insulin on Ischemic Brain Injury in Rat Hippocampus Through Negative Regulation of JNK Signaling Pathway to PI3K/Akt Activation," Brain Res., 1052(1), pp. 1-9 (2005).
Katoh et al., "Cross-Talk of WNT and FGF Signaling Pathways at GSK3β to Regulate β-Catenin and SNAIL Signaling Cascades," Cancer Biol. Ther., 5(9), pp. 1059-1064 (2006).
Kenney et al., "Hedgehog and PI-3 Kinase Signaling Converge on Nmyc1 to Promote Cell Cycle Progression in Cerebellar Neuronal Precursors," Development, 131(1), pp. 217-228 (2004).
Kiel et al., "SLAM Family Receptors Distinguish Hematopoietic Stem and Progenitor Cells and Reveal Endothelial Niches for Stem Cells," Cell, 121, pp. 1109-1121 (2005).
Kim et al., "GSK3 at the Edge: Regulation of Developmental Specification and Cell Polarization," Current Drug Targets, 7(11), pp. 1411-1419 (2006).
Kimura et al., "Conditional Loss of PTEN Leads to Testicular Teratoma and Enhances Embryonic Germ Cell Production," Development, 130, pp. 1691-1700 (2003).
Kirstetter et al., "Activation of the Canonical Wnt Pathway Leads to Loss of Hematopoietic Stem Cell Repopulation and Multilineage Differentiation Block," Nat. Immunol., 7 (10), pp. 1048-1056 (2006).
Kobayashi et al., "Thrombopoietin Supports Proliferation of Human Primitive Hematopoietic Cells in Synergy With Steel Factor and/or Interleukin-3," Blood, 88(2), pp. 429-436 (1996).
Komarov et al., "A Chemical Inhibitor of p53 That Protects Mice from the Side Effects of Cancer Therapy," Science, 285(5434), pp. 1733-1737 (1999).
Kondo et al., "Identification of Clonogenic Common Lymphoid Progenitors in Mouse Bone Marrow," Cell, 91, pp. 661-672 (1997).
Li et al., "Mechanistic Insights Into Maintenance of High p53 Acetylation by PTEN," Molecular Cell, 23, pp. 575-587 (2006).
Li et al., "Stem Cell Niche: Structure and Function," Annu. Rev. Cell Dev. Biol., 21, pp. 605-631 (2005).
Lopiccolo et al., "Targeting Akt in Cancer Therapy," Anticancer Drugs, 18(8), pp. 861-874 (2007).
Maehama et al., "The Tumor Suppressor, PTEN/MMAC1, Dephosphorylates the Lipid Second Messenger, Phosphatidylinositol 3,4,5-Trisphosphate," J. Biol. Chem., 273(22), pp. 13375-13378 (1998).
Maira et al., "Identification and Characterization of NVP-BEZ235, A New Orally Available Dual Phosphatidylinositol 3-Kinase/Mammalian Target of Rapamycin Inhibitor With Potent In Vivo Antitumor Activity," Mol. Cancer Ther., 7(7), pp. 1851-1863 (2008).
Matsuoka et al., "Fbxw7 Acts As a Critical Fail-Safe Against Premature Loss of Hematopoietic Stem Cells and Development of T-ALL," Genes & Development, 22, pp. 986-991 (2008).
Mayo et al., "A Phosphatidylinositol 3-Kinase/Akt Pathway Promotes Translocation of Mdm2 From the Cytoplasm to the Nucleus," PNAS, 98(20), pp. 11598-11603 (2001).
Mimeault et al., "Stem Cells: A Revolution in Therapeutics—Recent Advances in Stem Cell Biology and Their Therapeutic Applications in Regenerative Medicine and Cancer Therapies," Clinical Pharmacology & Therapeutics, 82, pp. 252-264 (2007).
Mise-Omata et al., "Transient Strong Reduction of PTEN Expression by Specific RNAi Induces Loss of Adhesion of the Cells," Biochem. Biophys. Res. Commun., 328(4), pp. 1034-1042 (2005).
Momand et al., "The Mdm-2 Oncogene Product Forms a Complex With the P53 Protein and Inhibits p53-Mediated Transactivation," Cell, 69(7), pp. 1237-1245 (1992).
Moon et al., "The Promise and Perils of Wnt Signaling Through β-Catenin," Science, 296(5573), pp. 1644-1646 (2002).
Mukhopadhyay et al., "Antisense Regulation of Oncogenes in Human Cancer," Crit. Rev. Oncog., 7(3-4), pp. 151-190 (1996).
Mutter, "PTEN, A Protean Tumor Suppressor," Am. J. Pathol., 158(6), pp. 1895-1898 (2001).
Nakorn et al., "Myeloerythroid-Restricted Progenitors Are Sufficient to Confer Radioprotection and Provide the Majority of Day 8 CFU-S," J. Clin. Invest., 109(12), pp. 1579-1585 (2002).
Nicholson et al., "The Protein Kinase B/Akt Signalling Pathway in Human Malignancy," Cellular Signalling, 14(5), pp. 381-395 (2002).
Nikitenko et al., "Adrenomedullin and Tumour Angiogenesis," British Journal of Cancer, 94, pp. 1-7 (2006).
North et al., "Prostaglandin E2 Regulates Vertebrate Haematopoietic Stem Cell Homeostatis," Nature, 447, pp. 1007-1011 (2007).
Novak et al., "Z/EG, A Double Reporter Mouse Line That Expresses Enhanced Green Fluorescent Protein Upon Cre-Mediated Excision," Genesis, 28, pp. 147-155 (2000).
Oren, "Decision Making by p53: Life, Death and Cancer," Cell Death and Differentiation, 10, pp. 431-442 (2003).
Pai et al., "Deoxycholic Acid Activates β-Catenin Signaling Pathway and Increases Colon Cell Cancer Growth and Invasiveness," Molecular Biology of the Cell, 15, pp. 2156-2163 (2004).
Paquette al., "Optimizing Hematopoietic Recovery Following Bone Marrow Transplantation," J. Clin. Invest., 109(12), pp. 1527-1528 (2002).
Park et al., "Bmi-1 Is Required for Maintenance of Adult Self-Renewing Haematopoietic Stem Cells," Nature, 423, pp. 302-305 (2003).
Perry et al., "Self-Renewal Versus Transformation: Fbxw7 Deletion Leads to Stem Cell Activation and Leukemogenesis," Genes & Development, 22, pp. 1107-1109 (2008).
Persad et al., "Tumor Suppressor PTEN Inhibits Nuclear Accumulation of Beta-Catenin and T Cell/Lymphoid Enhancer Factor 1-Mediated Transcriptional Activation," J. Cell Biol., 153(6), pp. 1161-1173 (2001).
Reya et al., "A Role for Wnt Signalling in Self-Renewal of Haematopoietic Stem Cells," Nature, 425, pp. 409-414 (2003).

Ring et al., "Selective Glycogen Synthase Kinase 3 Inhibitors Potentiate Insulin Activation of Glucose Transport and Utilization In Vitro and In Vivo," Diabetes, 52, pp. 588-595 (2003).

Salmena et al., "Tenets of PTEN Tumor Suppression," Cell, 133, pp. 403-414 (2008).

Saragovi et al., "Design and Synthesis of a Mimetic From an Antibody Complementarity-Determining Region," Science, 253(5021), pp. 792-795 (1991).

Sarbassov et al., "Phosphorylation and Regulation of Akt/PKB by the Rictor-mTOR Complex," Science, 307(5712), pp. 1098-1101 (2005).

Scheller et al., "Hematopoietic Stem Cell and Multilineage Defects Generated by Constitutive β-Catenin Activation," Nature Immunology, 7, pp. 1037-1047 (2006).

Schmid et al., "Bisperoxovanadium Compounds Are Potent PTEN Inhibitors," FEBS Letters, 556, pp. 35-38 (2004).

Song et al., "The Activation of Akt/PKB Signaling Pathway and Cell Survival," J. Cell. Mol. Med., 9(1), pp. 59-71 (2005).

Stein et al., "Oligodeoxynucleotides as Inhibitors of Gene Expression: A Review," Cancer Research, 48, pp. 2659-2668 (1998).

Stiles et al., "PTENless Means More," Developmental Biology, 273, pp. 175-184 (2004).

Suzuki et al., "T Cell-Specific Loss of Pten Leads to Defects in Central and Peripheral Tolerance," Immunity, 14, pp. 523-534 (2001).

Tamama et al., "Epidermal Growth Factor as a Candidate for Ex Vivo Expansion of Bone Marrow-Derived Mesenchymal Stem Cells," Stem Cells, 24, pp. 686-695 (2006).

Tang et al., "PTEN Autoregulates Its Expression by Stabilization of p53 in a Phosphatase-Independent Manner," Cancer Res., 66(2), pp. 736-742 (2006).

Tee et al., "Inactivation of the Tuberous Sclerosis Complex-1 and -2 Gene Products Occurs by Phosphoinositide 3-Kinase/Akt-Dependent and -Independent Phosphorylation of Tuberin," J. Biol. Chem., 278 (39), pp. 37288-37296 (2003).

Tessier et al., "Role of the Phox Homology Domain and Phosphorylation in Activation of Serum and Glucocorticoid-Regulated Kinase-3," J. Biol. Chem., 281(33), pp. 23978-23989 (2006).

Thornberry et al., "Caspases: Enemies Within," Science, 281(5381), pp. 1312-1316 (1998).

Tian et al., "Bridging the BMP and Wnt Pathways by PI3 Kinase/Akt and 14-3-3ζ," Cell Cycle, 4(2), pp. 215-216 (2005).

Van Der Krol et al., "Modulation of Eukaryotic Gene Expression by Complementary RNA or DNA Sequences," Biotechniques, 6(10), pp. 958-976 (1988).

Varnum-Finney et al., "Pluripotent, Cytokine-Dependent, Hematopoietic Stem Cells Are Immortalized by Constitutive Notch1 Signaling," Nature Medicine, 6(11), pp. 1278-1281 (2000).

Wen et al., "Negative Regulation of Phosphatidylinositol 3-Kinase and Akt Signalling Pathway by PKC," Cellular Signalling, 15, pp. 37-45 (2002).

West et al., "Rapid Akt Activation by Nicotine and a Tobacco Carcinogen Modulates the Phenotype of Normal Human Airway Epithelial Cells," J. Clin. Invest., 111(1), pp. 81-90 (2003).

White et al., "Negative Regulation of Myofibroblast Differentiation by PTEN (Phosphatase and Tensin Homolog Deleted on Chromosome 10)," Am. J. Respir. Crit. Care Med., 173, pp. 112-121 (2006).

Wu et al., "PTEN Signaling Pathways in Melanoma," Oncogene, 22, pp. 3113-3122 (2003).

Xie et al., "Detection of Functional Haematopoietic Stem Cell Niche Using Real-Time Imaging," Nature, p. 97-101 (2009).

Yacoub et al., "Optimized Production and Concentration of Lentiviral Vectors Containing Large Inserts," J. Gene Med., 9(7), pp. 579-584 (2007).

Yilmaz et al., "Pten Dependence Distinguishes Haematopoietic Stem Cells From Leukaemia-Initiating Cells," Nature, 441, pp. 475-482 (2006).

Ying et al., "The Ground State of Embryonic Stem Cell Self-Renewal," Nature, 453, pp. 519-523 (2008).

Zhang C. et al., "Murine Hematopoietic Stem Cells Change Their Surface Phenotype During Ex Vivo Expansion," Blood, 105(11), pp. 4314-4320 (2005).

Zhang J. et al., "BMP Signaling and Stem Cell Regulation," Developmental Biology, 284, pp. 1-11 (2005).

Zhang J. et al., "Identification of the Haematopoietic Stem Cell Niche and Control of the Niche Size," Nature, 425, pp. 836-841 (2003).

Zhang J. et al., "PTEN Maintains Haematopoietic Stem Cells and Acts in Lineage Choice and Leukaemia Prevention," Nature, 441, pp. 518-522 (2006).

Zhang et al., "Angiopoietin-like Proteins Stimulate Ex Vivo Expansion of Hematopoietic Stem Cells," Nat. Med., 12(2), pp. 240-245 (2006).

Zhang Q et al., "Small-Molecule Synergist of the Wnt/β-Catenin Signaling Pathway," PNAS, 104(18), pp. 7444-7448 (2007).

Zhu et al., "A Versatile Approach to Multiple Gene RNA Interference Using MicroRNA-Based Short Hairpin RNAs," BMC Molecular Biology, 8(98), pp. 1-11 (2007). (p. No. not for citation purposes).

Groszer et al., "Negative Regulation of Neural Stem/Progenitor Cell Proliferation by the Pten Tumor Suppressor Gene in Vivo," Science, 294, pp. 2186-2189 (2001).

Liu et al., "A Small-Molecule Agonist of the Wnt Signaling Pathway," Angewandte Chemie International Edition, 44 (13), pp. 1987-1990 (2005).

Borowitz et al., "Immunophenotyping of acute leukemia by flow cytometric analysis," Am. J. Clin. Pathol., 100, pp. 534-540 (1993).

Non-Final Office Action mailed May 8, 2012 in U.S. Appl. No. 12/589,551 (Paper No. 20120505).

Hofmeister et al., "*Ex Vivo Expansion of Umbilical Cord Blood Stem Cells for Transplantation: Growing Knowledge From the Hematopoietic Niche*," Bone Marrow Transplantation, 39, pp. 11-23 (2007).

Trowbridge et al., "*Glycogen Synthase Kinase-3 is an in Vivo Regulator of Hematopoietic Stem Cell Repopulation*," Nature Medicine, vol. 12, No. 1, pp. 89-98 (2006).

* cited by examiner

A

B

Pten

Pten:Ctnnb1

\* P < 0.01

D

J

METHODS AND COMPOSITIONS FOR STEM CELL SELF-RENEWAL

RELATED APPLICATIONS

This application is the National Stage of International Application No. PCT/US2008/005230, filed Apr. 23, 2008, which claims benefit to U.S. Provisional Patent Application Ser. No. 60/926,065, filed Apr. 23, 2007 and U.S. Provisional Patent Application Ser. No. 61/066,693, filed Feb. 22, 2008, which applications are incorporated by reference in their entirety.

FIELD OF THE INVENTION

The present invention relates to methods and compositions for expanding a stem cell population, particularly an hematopoietic stem cell population.

BACKGROUND OF THE INVENTION

Hematopoietic stem cells (HSCs) are clonogenic cells, which possess the properties of both self-renewal (expansion) and multilineage potential giving rise to all types of mature blood cells. HSCs are responsible for hematopoiesis and undergo proliferation and differentiation to produce mature blood cells of various lineages while still maintaining their capacity for self-renewal. The ability to self-renew maintains the HSC population for the lifespan of an animal and also allows HSCs to repopulate the bone marrow of lethally irradiated congenic hosts.

Early HSC development displays a hierarchical arrangement, starting from long-term (LT-) HSCs, which have extensive self-renewal capability, followed by the expansion state, which corresponds to short-term (ST-) HSCs (having limited self-renewal ability) and proliferative multipotent progenitors (MPPs) (having multipotent potential but no self-renewal capability). MPP is also a stage of priming or preparation for differentiation. An MPP differentiates and commits to become either a common lymphoid progenitor (CLP), which gives rise to all the lymphoid lineages, or a common myeloid progenitor (CMP), which produces all the myeloid lineages. During this process, the more primitive population gives rise to a less primitive population of cells, which is unable to give rise to a more primitive population of cells. The intrinsic genetic programs that control these processes including the multipotential, self-renewal, and activation (or transient amplification) of HSCs, and lineage commitment from MPP to CLP or CMP, remain largely unknown.

To sustain constant generation of blood cells for the lifetime of an individual, HSCs located in bone marrow niches (Zhang, J. et al. *Nature* 425, 836-841, 2003; Calvi, L. M. et al. *Nature* 425, 841-846, 2003; Kiel, M. J., et al. *Cell* 121, 1109-1121, 2005; Arai, F. et al. *Cell* 118, 149-161, 2004) must achieve a balance between quiescence and activation so that immediate demands for hematopoiesis are fulfilled, while long-term stem cell maintenance is also assured. In adults, homeostasis between the quiescent and activated states of stem cells is important to protect HSCs from losing their potential for self-renewal and, at the same time, support ongoing tissue regeneration (Li, L. and Xie, T. *Annu. Rev. Cell. Dev. Biol.* 21, 605-631, 2005). Over-activation and expansion of stem cells risks both eventual depletion of the stem cell population and a predisposition to tumorigenesis. Although some factors important for stem cell activation have been identified (Heissig, B. et al. *Cell* 109, 625-637, 2002), the molecular events governing the transition between quiescence and activation are poorly understood.

Phosphatase and tensin homolog (PTEN) functions as a negative regulator of the PI3K/Akt pathway, which plays crucial roles in cell proliferation, survival, differentiation, and migration (Stiles, B. et al. *Dev. Biol.* 273, 175-184, 2004). The PTEN tumor suppressor is commonly mutated in tumors, including those associated with lymphoid neoplasms, which feature deregulated hematopoiesis (Mutter, G. L. *Am. J. Pathol.* 158, 1895-1898, 2001; Suzuki, a. et al. *Immunity* 14, 523-534, 2001). PTEN-deficiency has been associated with expansion of neural and embryonic stem cell populations (Groszer, M. et al. *Science* 294, 2186-2189, 2001; Kimura, T. et al. *Development* 130, 1691-1700, 2003). But, the role of PTEN in stem cells and tumorigenesis and the recurrence of tumors heretofore has been not understood.

PTEN functions as an antagonist of phosphatidyl inositol 3-kinase (PI3K) (Maehama T & Dixon J E. *J Biol. Chem.* 273:13375-13378. 1998). The serine kinase Akt is downstream of the PI3K signal (Cross D A, Alessi D R, Cohen P et al. *Nature* 378:785-789 1995). PTEN has been shown to inhibit Akt and thereby inhibit the nuclear accumulation of β-catenin (Persad S et al. *J Cell Biol.* 153:1161-1174 2001).

Akt has a broad range of effects. Its major function is to provide a survival signal and to block apoptosis, complementary to its regulation of β-catenin function. (Song, G. et al., *J. Cell. Mol. Med.*, 9 (1): 59-71, 2005) Akt acts through a number of proteins, including mammalian target of rapamycin (mTOR), the Forkhead family of transcription factors (FoxO), BAD, caspase 9, murine double minute 2 (Mdm2).

Akt can directly and indirectly activate the serine/threonine kinase mTOR, which activates protein translation through a signaling cascade. (LoPiccolo, J., et al., Anti-Cancer Drugs, 18:861-874, 2007). Indirect activation occurs through tuberous sclerosis complex-2 (TSC2), which, when in the unphosphorylated state, forms a complex with tuberous sclerosis complex-1 (TSC1, also known as hamartin). This complex promotes the GTPase activity of Ras homolog enriched in brain (RHEB), which in turn, acts to down-regulate mTOR activity. Upon phosphorylation by Akt, however, the ability of the TSC1-TSC2 complex to promote RHEB's GTPase activity is inhibited, and therefore, mTOR's activity is promoted. (Cully, M. et al., Nat. Rev. Cancer, 6:184-192, 2006). mTOR can also form a complex with Rictor, and this complex can provide positive feedback on the Akt signaling cascade by phosphorylating and activating Akt. (Sarbassov, D. D., et al., Science, 307: 1098-1101, 2005).

Akt also regulates cell survival through transcriptional factors, including FoxO. Akt's phosphorylation of FoxO inhibits FoxO, resulting in inhibition of transcription of several proapoptotic genes, such as Fas-L, IGFBP1 and Bim. (Datta, S. R., et al., Cell, 91:231-241, 1997; Nicholson, K. M., et al., Cell Signal, 14:381-395, 2002).

One of the down-stream targets of FoxO is p27 (Kip1), a potent inhibitor of cyclin E/cdk2 complexes. (Wu, H. et al., Oncogene, 22: 3113-3122, 2003). FoxO factors induce expression of p27, which can bind to cyclin E/cdk2 complexes and inhibit their activity, resulting in a block in cellular proliferation. (Burgering, B. M. T. & Medema, R. H., J. Leukocyte Biol., 73:689-701, 2003). In addition, Akt itself can also directly phosphorylate p27 on T157, resulting in the redistribution of p27 from the nucleus to the cytoplasm, away from cyclin E/cdk2 complexes. (Id.) Phosphorylation of p27 on T198 was critical for the binding of p27 to 14-3-3 proteins, and through this pathway, Akt may directly promote p27's degradation. (Fujita, N., et al., J. Biol. Chem., 277 (32): 28706-28713, 2002).

Another one of the targets of Akt in promoting cell survival is BAD, a member of the Bcl-2 family of proteins. In the absence of Akt phosphorylation, BAD forms a complex with Bcl-2 or Bcl-X on the mitochondrial membrane and inhibits the anti-apoptotic potential of Bcl-2 and Bcl-X. (Song, G. et al., J. Cell. Mol. Med., 9 (1): 59-71, 2005) Akt phosphorylates BAD on Serine 136, thus releasing BAD from the Bcl-2/Bcl-X complex. (Song, G. et al., J. Cell. Mol. Med., 9 (1): 59-71, 2005; Datta, S. R., et al., Genes Dev., 13:2905-2927, 1999). Therefore, Akt suppresses BAD-mediated apoptosis and promotes cell survival.

Furthermore, by phosphorylation of pro-caspase-9 at Serine 196, Akt inhibits proteolytic processing of pro-caspase-9 to the active form, caspase-9, which is an initiator and an effecter of apoptosis (Cardone et al., 1998, Science, 282: 1318-1320, Donepudi, M. & Gruner, M. G., Biophys. Chem., 145-152, 2002).

Additionally, Akt regulates cell survival via the Mdm2/p53 pathway. Akt can activate Mdm2 by direct phosphorylation, thereby inducing the nuclear import of Mdm2 or the up-regulation of Mdm2's ubiquitin ligase activity. (Mayo L. D., Donner D. B., 2001, Proc. Natl., Acad. Sci. USA 98:11598-11603; Gottlieb T. M. et al, Ocogene, 21: 1299-1303, 2002). Mdm2 negatively regulates the p53 protein, which may induce cell death in response to stresses (Oren M., Cell Death Differ., 10:431-442, 2003), by targeting p53 for ubiquitin-mediated proteolysis (Haupt, Y. et al., 1997, Nature 387: 296-299) or by binding to the transactivation domain of p53, thereby inhibiting p53-mediated gene regulation. (Momand, J. et al., Cell, 69: 1237-1245, 1992) One of the down-stream targets of p53 is the p21 (CIP1/WAF1) gene. The p53 gene product binds to a site located 2.4 kb upstream of the p21 coding sequence, and this binding site confers p53-dependent transcriptional regulation. (El-Deiry, W. S., et al., Cell, 75: 817-825, 1993) Thus, down-regulation of p53 also down-regulates the transcription of p21.

PTEN not only regulates p53 protein through antagonizing the Akt-Mdm2 pathway, it can also directly regulate p53. First, PTEN can enhance p53 transactivation in a phosphatase-independent manner (Tang, Y. & Eng C., Cancer Research, 66: 736-742, 2006). Second, PTEN forms a complex with p300 in the nucleus and plays a role in maintenance of high p53 acetylation, which is the activated form of p53. (Li A. et al., Molecular Cell, 23 (4): 575-587, 2006). In turn, p53 may also activate the transcription of PTEN. (Cully, M. et al., Nat. Rev. Cancer, 6:184-192, 2006).

Canonical signals in the Wnt pathway are involved in stem cell proliferation. (Kim, L. & Kimmel, A. R. *Current Drug Targets* 7:1411-1419, 2006). Glycogen synthase kinase 3 beta (GSK-3β) is a part of the Wnt signaling pathway, and its primary substrate is β-catenin. (Hagen, T et al., *J. Biochem.* 277 (26):23330-23335). In the absence of canonical Wnt signaling, GSK-3β binds to β-catenin and phosphorylates β-catenin, thereby targeting β-catenin for ubiquitination and followed by proteosome-mediated degradation, which is mediated by Adenomatous Polyposis Coli (APC). (Id., Moon, R. T. et al., *Science* 296:1644-1646. 2002). Canonical Wnt signals induce the release of β-catenin from GSK-3β, thereby activating β-catenin. (Katoh, M & Katoh, M. *Cancer Biol Ther.* 5 (9):1059-64, 2006). β-catenin then localizes to the nucleus, where it activates gene transcription. (Id.).

In sum, individually it was known or suggested that modulating GSK-3β and PTEN could promote stem cell, e.g., HSC, proliferation. But, such knowledge and speculation was insufficient to provide a clinically useful approach to expanding a stem cell population for subsequent transplantation and reconstitution of the engrafted cell lineage.

In view of the foregoing, it would be advantageous to elucidate the interaction between Wnt and PTEN signaling pathways and to provide new insights into molecular regulation of stem cell proliferation and differentiation. It would also be advantageous to use such insights to provide new methods and compositions for expanding stem cells in vivo and ex vivo, which stem cells would be of the kind and quantity sufficient to transplant into a suitable recipient.

SUMMARY OF THE INVENTION

Thus, one embodiment of the invention is a method for expanding a population of stem cells obtained from a tissue selected from the group consisting of peripheral blood, cord blood, and bone marrow. This method comprises modulating a PTEN pathway and a Wnt pathway in the population of stem cells to expand the number of stem cells.

Another embodiment of the invention is a method for ex vivo expansion of a substantially undifferentiated stem cell population. This method comprises modulating a PTEN pathway and a Wnt pathway in the undifferentiated stem cell population to expand the number of undifferentiated stem cells without significant differentiation of the stem cell population.

Yet another embodiment of the invention is a method for ex vivo expansion of an hematopoietic stem cell (HSC) population obtained from a tissue selected from the group consisting of peripheral blood, cord blood, and bone marrow. This method comprises modulating a PTEN pathway and a Wnt pathway in the HSC population to expand the HSC population to a sufficient quantity while maintaining a multilineage differentiation potential in the HSC population, which is sufficient for subsequent transplantation into a patient in need thereof.

Another embodiment of the invention is an expanded, substantially undifferentiated stem cell population made by a method of the present invention. In a related embodiment, the invention is an expanded HSC population made by a method of the present invention.

An additional embodiment is a method for ex vivo expansion of hematopoietic stem cells (HSCs) by at least 40-fold, the expanded HSCs being competent to reconstitute an HSC lineage upon transplantation into a mammalian patient in need thereof. This method comprises culturing a population of HSCs in a suitable culture medium comprising a PTEN inhibitor and a GSK-3β inhibitor.

A further embodiment of the invention is a kit for expanding an hematopoietic stem cell (HSC) population for subsequent transplantation into a patient in need thereof. The kit comprises a PTEN inhibitor, a GSK-3β inhibitor, and instructions for the use of the inhibitors.

An additional embodiment is a media for carrying out ex vivo expansion of a stem cell population. The media comprises a fluid media suitable for maintaining viable stem cells and PTEN and GSK-3β inhibitors present in the media at concentrations sufficient to enable expansion of the stem cell population while maintaining a multilineage differentiation potential in the stem cells.

Yet another embodiment is a method for administering an hematopoietic stem cell (HSC) to a patient in need thereof. This method comprises (a) culturing, in a suitable culture media, a sample containing an HSC population in the presence of a modulator of a molecule in the PTEN pathway and a modulator of a molecule in the Wnt pathway for a period of time sufficient to expand the number of HSCs in the sample to a number sufficient to transplant into the patient; (b) removing from the culture the PTEN and Wnt pathway modulators; and (c) administering the HSCs to the patient.

A further embodiment of the invention is a method for reconstituting bone marrow in a patient in need thereof. This method comprises: (a) culturing, in a suitable culture media, a sample containing an HSC population in the presence of a modulator of a molecule in the PTEN pathway and a modulator of a molecule in the Wnt pathway for a period of time sufficient to expand the number of HSCs in the sample to a number sufficient to transplant into the patient; (b) removing from the culture the PTEN and Wnt pathway modulators; and (c) administering the HSCs to the patient.

Another embodiment is a method for expanding a population of hematopoietic stem cells (HSCs). This method comprises culturing a population of HSCs under conditions sufficient to result in an expansion of the HSC population by at least 40-fold, wherein the expanded population of HSCs is suitable for transplantation into a mammal in need thereof.

Yet another embodiment is a method for treating a patient in need of a transplant selected from the group consisting of a bone marrow transplant, a peripheral blood transplant, and an umbilical cord blood transplant. This method comprises administering to the patient a population of HSCs obtained by a method of the present invention.

A further embodiment is a method for expanding a population of hematopoietic stem cells (HSCs) comprising: (a) obtaining from a mammal a tissue sample comprising an HSC population; (b) expanding, in vitro, the HSC population from the sample, wherein: (i) the HSC population expands by at least 40-fold; and (ii) the expanded HSC population has the ability to reconstitute an hematopoietic lineage for at least 4-weeks after transplantation into a recipient.

An additional embodiment is a method for reconstituting an hematopoietic stem cell lineage in a recipient in need thereof. This method comprises: (a) obtaining from a mammal a tissue sample comprising an HSC population; (b) expanding, in vitro, the HSC population from the sample, wherein: (i) the HSC population expands by at least 40-fold; and (ii) the expanded HSC population has the ability to reconstitute an hematopoietic lineage for at least 4-weeks after transplantation into a recipient in need thereof; and (c) transplanting the expanded HSC population into a recipient in need thereof.

A further embodiment of the invention is a method for expanding a hematopoietic stem cell population in a mammal in need of such expansion. This method comprises administering to the mammal a therapeutically effective amount of a modulator of Wnt and Akt for a period of time sufficient to expand the HSC population by at least 40-fold with HSCs that possess the ability to reconstitute an hematopoietic lineage in the mammal.

These and other aspects of the invention are further disclosed in the detailed description and examples which follow.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A is two bar graphs showing the absolute numbers (per femur+tibia) of lineage negative, Sca-1$^+$Kit$^+$ (LSK) cells in Scl-Cre negative control and Scl-Cre$^+$ PTEN with constitutively activated β-catenin (Pten:Ctnnb1) double mutant and each single mutant bone marrow (top) and spleen (bottom) as determined by FACS analysis. (Harada, N., et al., $Embo\ J$, 18 (21): 5931-42 1999. Yilmaz, O. H., et al., $Nature$, 441:475-82 2006. Zhang, J., et al., $Nature$, 441 (7092): 518-22 2006.) Mice are at 10 days post-induction of Tamoxifen. Reduction of LSK cells in double mutant bone marrow with expansion in the spleen is indicative of mobilization from bone marrow to spleen. Scl-Cre is an HSC-specific Tamoxifen inducible Cre-recombinase used to achieve conditional knockout of LoxP flanked (floxed) Pten and Ctnnb1 alleles. (Gothert, J. R., et al., $Blood$, 105 (7): 2724-2732, 2005.)

FIGS. 1B-1E show representative results of FACS analysis of lineage negative, Sca-1$^+$Kit$^+$ (LSK) cells in Scl-Cre negative control (B and D) and Scl-Cre$^+$ PTEN with constitutively activated β-catenin (Pten:Ctnnb1) double mutant (C and E) bone marrow and spleen as indicated. Boxes on the left show Sca-1$^-$Kit$^+$ (early hematopoietic progenitor cells), and boxes on the right show Sca-1$^+$Kit$^+$ (LSK) cells. Cells were pre-gated on live, lineage negative cells. Cells were collected from mice at 6 weeks post-induction of Tamoxifen.

FIGS. 1F and G are bar graphs showing the absolute number of LSK cells per femur and tibia in control, Ctnnb1, Pten, and Pten:Ctnnb1 double mutant bone marrow (F) and spleen (G) at 6 weeks post-induction. While the percentage of LSKs is increased in double mutants (see FIG. 1C), low cellularity of bone marrow from double mutants yields only moderately increased absolute numbers compared to control.

FIGS. 1H and I are bar graphs and FACS analysis, respectively, of percentage of LSK cells, which are Flk2$^-$ (indicating long-term reconstituting (LT)-HSCs) in control, Ctnnb1, Pten, and Pten:Ctnnb1 mutant bone marrow at 6 weeks post-induction. Ctnnb1 single mutants are not significantly different from controls at this time point (data not shown). Boxes in FIG. 1I indicate Flk2$^-$ (LT HSC) cells.

FIG. 1J is a set of FACS analyses of CD45 in leukemic Pten:Ctnnb1 mutant bone marrow. CD45 (high) blast crisis cells are indicated (blue box, left panel). No blast cell population is observed in control or Ctnnb1 mutants while a minor population has been observed in 1 of 1 Pten single mutant mice at 6 weeks post-induction (data not shown). The right panel shows LSK analysis of leukemic Pten:Ctnnb1 mutant mouse bone marrow. Note the conversion to blast cells (lower left) with only a remnant LSK population (compare to FIG. 1C).

FIG. 1K is a bar graph showing early hematopoietic progenitors defined by FACS analysis in control, Ctnnb1, Pten, and Pten:Ctnnb1 double mutant bone marrow. Common myeloid progenitor (CMP); granulocyte-monocyte progenitor (GMP); megakaryocyte-erythrocyte progenitor (MEP); and common lymphoid progenitor (CLP).

FIG. 2A is a series of photographs showing 100 LSK cells isolated from control, active β-catenin (Ctnnb1), Pten mutant, and double mutant (Pten:Ctnnb1) mice after 10 days in culture (original magnification 100×). Cell numbers are not dramatically increased from 100 seeded LSKs in control while Ctnnb1 single mutant LSKs do not survive. In contrast, Pten single mutant LSKs exhibit greater proliferation but appear more heterogeneous indicating more significant differentiation. The greatest and most homogeneous expansion occurs from Pten:Ctnnb1 double mutant LSKs.

FIG. 2B is a set of photographs showing LSK cells from Pten and Pten:Ctnnb1 mutants at 34 days culture (original magnification 200×). (Note: wild-type control cultures do not expand beyond 4 weeks; Ctnnb1 mutant cultures do not survive beyond 10 days.) Pten mutant HSC cultures appear more heterogeneous with significant cell clumping and more irregular cell morphology. Also note the spindle-shaped adherent cells (arrows) showing differentiation. In contrast, double mutant HSC cultures exhibit consistent morphology. Therefore, while Pten single mutant LSKs survive and expand, they have undergone more significant differentiation than the much more homogeneous Pten:Ctnnb1 double mutant LSKs.

FIGS. 2C and D are bar graphs showing the results of an expansion experiment. Pten and Pten:Ctnnb1 LSK seven week cultures were counted and analyzed by FACS for maintenance of the LSK phenotype (wild-type control and Ctnnb1 cultures did not survive this long in vitro). Double mutant LSKs undergo >1,200 fold expansion vs. 50 fold for Pten single mutant LSKs. LSK purity of cultures is significantly greater in Pten:Ctnnb1 cultures maintaining the LSK phenotype in about 85% of total live cells vs. about 50% for Pten single mutant cultures.

FIG. 2E is a FACS analysis of a 7 week culture of Pten:Ctnnb1 LSK cells (pre-gated on live, lineage negative cells). The boxed area indicates Kit$^+$Sca-1$^+$ (LSK) cells.

FIGS. 2F and G are FACS analyses showing a transplant engraftment experiment. At 5 weeks culture (see FIG. 2B), Pten and Pten:Ctnnb1 LSK cultures were re-sorted and 1000 LSK cells (CD45.2$^+$) from each were transplanted into lethally irradiated (10Gy) CD45.1$^+$ recipient mice along with 2×10$^5$ congenic whole bone marrow competitor cells. Because wild-type cells did not survive 5 weeks culture, 1000 fresh wild-type LSK cells were also transplanted as a separate control group. At 4 weeks post-transplant, there was no detectable engraftment from peripheral blood analysis of mice transplanted with either Pten or Pten:Ctnnb1 LSK cultures (data not shown). At 5 weeks post-transplant, bone marrow from recipient mice was analyzed for donor engraftment (CD45.2$^+$ cells) and donor LSK cells (CD45.2$^+$ LSKs). FIGS. 2F and G display representative donor engraftment (left, boxed areas indicate CD45.2$^+$ donor cells) and donor LSK cell engraftment (right, boxed areas indicate LSK cells) from bone marrow of mice transplanted with 1000 Fresh LSK cells (F) or 1000 cultured Pten:Ctnnb1 LSK cells (G).

FIGS. 2H-J are bar graphs showing the quantitative analysis of donor (CD45.2$^+$) cells (H), donor LSK cells (I), and fold increase in donor LSKs (J) isolated from bone marrow of recipient mice described in FIGS. 2F and 2G at 5 weeks post-transplant.

FIG. 3A is a schematic illustrating representative members of the Wnt and PTEN pathways. Inhibition of GSK-3β leads to β-catenin activation which blocks HSC differentiation. Inhibition of PTEN leads to Akt activation which promotes survival. Both pathways individually have been shown to promote HSC proliferation.

FIGS. 3B and C are photographs of HSCs. One hundred LSK Flk2$^-$ cells were sorted from wild-type (C57Bl/6) mice and cultured in (1) media, (2) media+1 μM CHIR99021 (GSK-3β inhibitor), (3) media+200 nM Dipotassium Bisperoxo(picolinato)oxovanadate (BpV(pic), a PTEN inhibitor), and (4) media+1 μM CHIR99021+200 nM BpV(pic). An alternative PTEN inhibitor, Shikonin, was also utilized at 200 nM alone (5) or in combination with 1 μM CHIR99021 (6). Pictures are at 17 days culture (B, original magnification 100×) and 23 days (C, original magnification 40×). Compared to control, both inhibitors applied individually yield greater expansion of LSK cells indicating that GSK-3β inhibition is not strictly equivalent to constitutive activation of β-catenin shown in Ctnnb1 mutant LSKs while BpV(pic) yields similar results compared to Pten mutant LSKs (see FIG. 2). Similar to double mutant LSKs (FIG. 2), the greatest expansion is shown with both inhibitors present (FIG. 3B/C, panel 4).

FIG. 3D is a series of photographs showing LSK Flk2$^-$ cells at 28 days culture in the indicated media conditions (original magnification 200×). Here, significant expansion relative to control is observed with both inhibitors present individually; however, significant differentiation/heterogeneity of cell morphology is observed in both single inhibitor cultures, including more variable cell size/morphology and/or differentiation to adherent, spindle-shaped cells (middle panels). In contrast, and quite surprisingly, expansion with homogeneity is achieved when both inhibitors are present (last panel).

FIG. 3E is a FACS analysis of 28 day LSK Flk2$^-$ cells cultured in media containing both inhibitors (200 nM BpV(pic) and 1 μM CHIR99021). Cells were pre-gated on live, lineage negative cells. The boxed area indicates Kit$^+$Sca1$^+$ (LSK) cells. Greater than 90% of LSKs retain Flk2 negativity (data not shown). The LSK Flk2$^-$ phenotype is maintained with high purity in cultures containing both inhibitors.

FIG. 3F is a bar graph showing fold expansion of LSK Flk2$^-$ cells after 28 days culture in the indicated conditions. While both inhibitors added individually lead to significant expansion compared to media without either inhibitor, the greatest expansion (~270 fold) is observed when both inhibitors are added together.

FIGS. 3G and H are bar graphs showing the % repopulation and % CD45.2$^+$ cells from engrafted mice. Twenty-eight day cultures (FIGS. 3 D-F) were re-sorted for LSK Flk2$^-$ cells and 1000 LSK Flk2$^-$ cells (CD45.2$^+$) from each media condition were transplanted into lethally irradiated (10Gy) CD45.1$^+$ recipient mice along with 2×10$^5$ congenic whole bone marrow competitor cells. At 4 weeks post-transplant, peripheral blood was analyzed for donor (G) and multi-lineage (H) engraftment. In FIG. 3G, each bar represents an individual mouse; the horizontal-dashed line represents the average "engraftment" of mice transplanted with competitor cells only and thus the limit of detectability for true engraftment. Long-term (4 month) engraftment has not been observed from 28-day cultures (data not shown). 6 of 8 mice show >1% engraftment when transplanted with LSK Flk2$^-$ cells cultured with both inhibitors present compared to 4/8 with only CHIR99021 present, 0/10 with only BpV(pic) present, and 2/6 with media only. One percent or greater engraftment is a standard limit for substantial engraftment. (Zhang, C. C., et al., *Nat Med*, 12 (2): 240-5, 2006. Zhang, C. C. and H. F. Lodish, *Blood*, 105 (11): 4314-20, 2005.) Thus, while use of both inhibitors together leads to greatest expansion in LSKs (FIG. 3F), transplantation of equivalent numbers of these cultured LSK Flk2$^-$ cells also yields increased short-term engraftment/functionality when cultured with both inhibitors compared to no or either single inhibitor only.

FIG. 3I is a bar graph showing the fold expansion of LSK Flk2$^-$ cells after 9 days culture in (1) media, (2) media+200 nM BpV(pic), (3) media+100 nM CHIR99021, and (4) media+200 nM BpV(pic)+100 nM CHIR99021. Because long-term engraftment was not observed from 28 day cultures (FIG. 3D-H and data not shown), LSK Flk2⁻ cells were cultured for only 9 days to test if both expansion and long-term repopulation can be achieved. Similar trends are observed here to the 28 day cultures (compare to FIG. 3F) although the extent of expansion is substantially reduced at only 9 days compared to 28 days culture.

FIG. 3J is a FACS analysis of 9 day LSK Flk2⁻ cells cultured in media+200 nM BpV(pic)+100 nM CHIR99021. The boxed area indicates Kit⁺Sca-1⁺ (LSK) cells. Cells were pre-gated on live, lineage negative cells. Greater than 90% of LSKs retain Flk2 negativity (data not shown). Here, the levels of Sca-1 and Kit appear normal compared to the Sca-1$^{(high)}$ Kit$^{(high)}$ population shown from 28 day cultures (FIG. 3E).

FIG. 3K is a bar graph showing % repopulation of 10-day cultured cells in mice. Ten day cultures were transplanted into lethally irradiated (10Gy) CD45.1⁺ recipient mice along with $2\times10^5$ congenic whole bone marrow competitor cells. The total, non-adherent cell product after 10 days culture of 100 initial LSK Flk2⁻ cells was transplanted per mouse. At 8 weeks post-transplant, peripheral blood was analyzed for donor engraftment. As in FIG. 3H, multi-lineage reconstitution was observed from all mice exhibiting true engraftment (data not shown). Each bar represents an individual mouse; the horizontal-dashed line represents the average 'engraftment' of mice transplanted with competitor cells only and thus the limit of detectability for true engraftment. Here, 3/7 mice transplanted with LSK Flk2⁻ cells cultured in the presence of both inhibitors exhibited 1% or greater donor engraftment vs. no mice reaching this threshold in the single or no inhibitor groups.

DETAILED DESCRIPTION OF THE INVENTION

One embodiment of the invention is a method for expanding a population of stem cells obtained from a tissue selected from the group consisting of peripheral blood, cord blood, and bone marrow. This method comprises modulating a PTEN pathway and a Wnt pathway in the population of stem cells to expand the number of stem cells.

As used herein, "expand", "expanding" and like terms means to increase the number of stem cells in the population relative to the number of stem cells in the original population either in vivo or ex vivo using any of the methods disclosed herein. Preferably, the expansion is at least 40-fold compared to the original number of stem cells in the population. More preferably, the expansion is at least 80-fold, 100-fold, 150-fold, 200-fold, 250-fold, or 270-fold compared to the original number of stem cells.

In the present invention "a population of stem cells" means a group of substantially undifferentiated cells that possess the ability to give rise to many different types of cells and which have the ability to self-renew. Representative, non-limiting examples of stem cells according to the present invention include bronchioalveolar stem cells (BASCs), bulge epithelial stem cells (bESCs), corneal epithelial stem cells (CESCs), cardiac stem cells (CSCs), epidermal neural crest stem cells (eNCSCs), embryonic stem cells (ESCs), endothelial progenitor cells (EPCs), hepatic oval cells (HOCs), hematopoetic stem cells (HSCs), keratinocyte stem cells (KSCs), mesenchymal stem cells (MSCs), neuronal stem cells (NSCs), pancreatic stem cells (PSCs), retinal stem cells (RSCs), and skin-derived precursors (SKPs).

Hematopoietic stem cells, for example, have the ability to self-renew (i.e., expand) and can give rise to all the types of progenitor cells (such as, e.g., CMP, GMP, MEP and CLP) and ultimately all the types of blood cells (such as e.g., red blood cells, B lymphocytes, T lymphocytes, natural killer cells, neutrophils, basophils, eosinophils, monocytes, macrophages, and platelets) in the hematopoietic system.

In the present invention, "modulating", "modulation" and like terms mean altering the signal transduction pathway, e.g., a protein in the PTEN and/or Wnt pathways, including but not limited to lowering or increasing the expression level of a protein, altering the sequence of such a protein (by mutation, pre-translational or post-translational modification or otherwise), or inhibiting or activating such a protein (whether by binding, phosphorylation, glycosylation, translocation or otherwise). Such modulation may be achieved genetically or pharmacologically.

Figure 3:
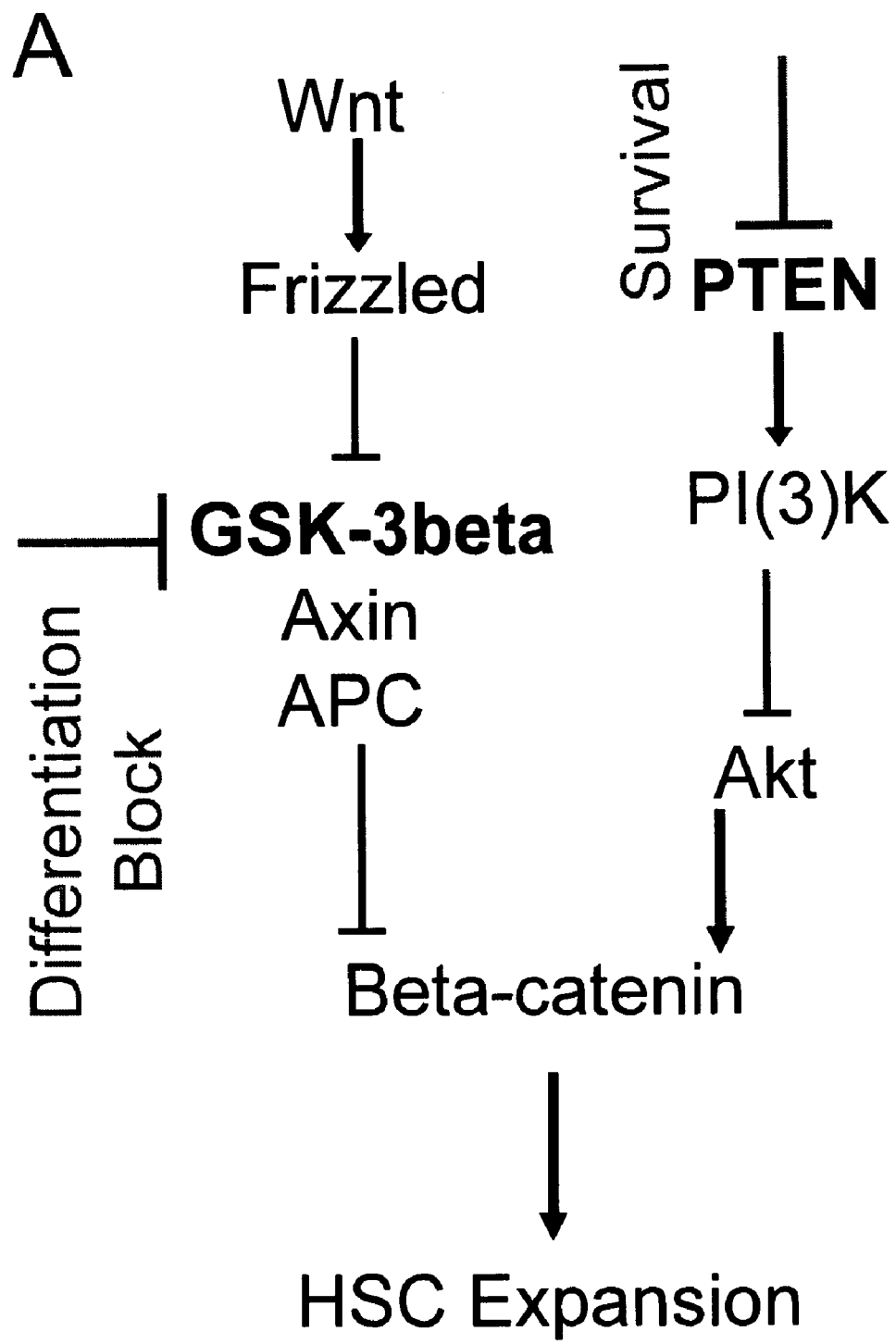
FIGS. 3A-K are schematics, photographs, bar graphs, and FACS analyses demonstrating that ex vivo pharmacological manipulation of the PTEN/Akt and Wnt/β-catenin signaling pathways cooperatively drive functional HSC expansion.
Figure 3:
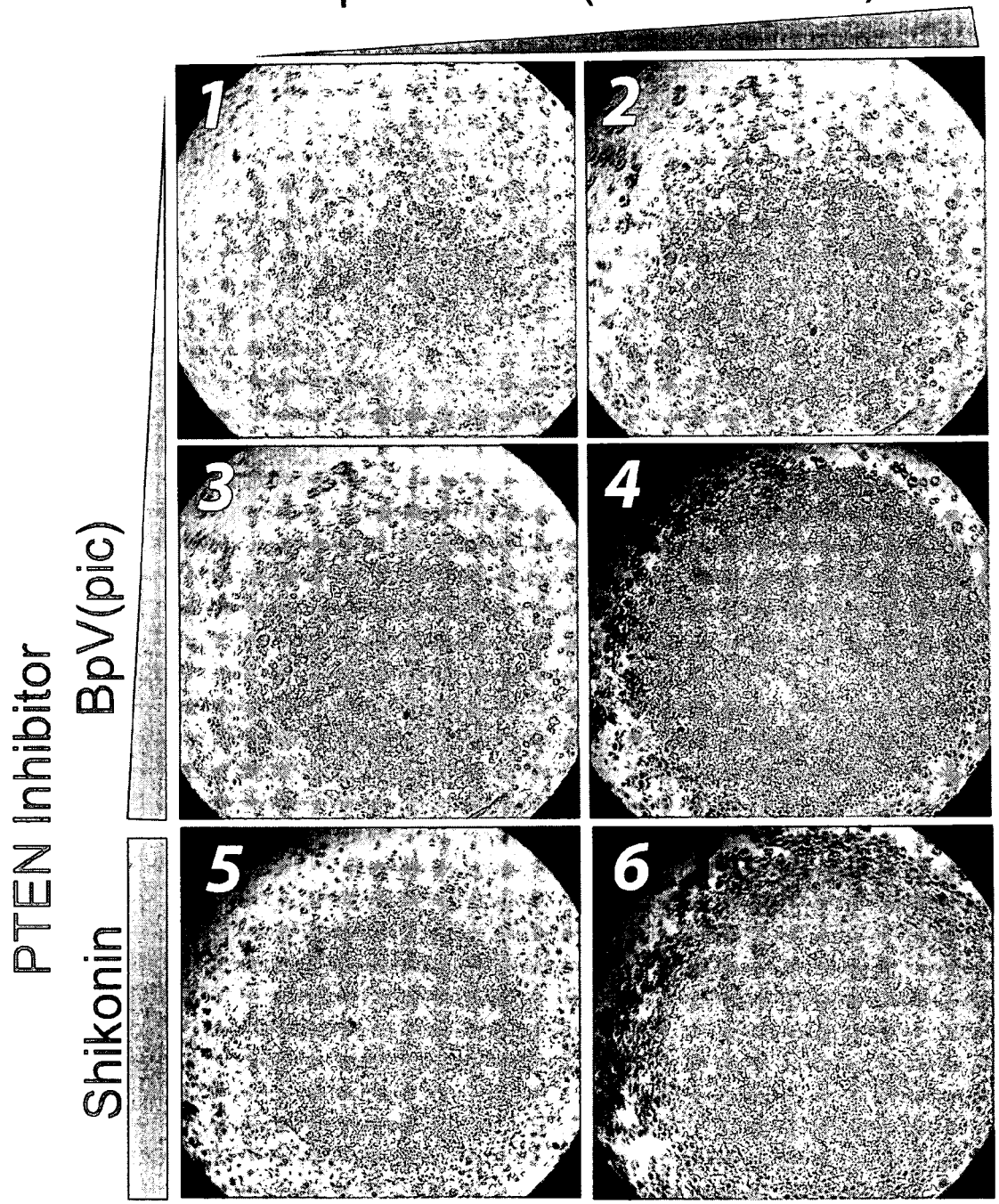
Figure 3:
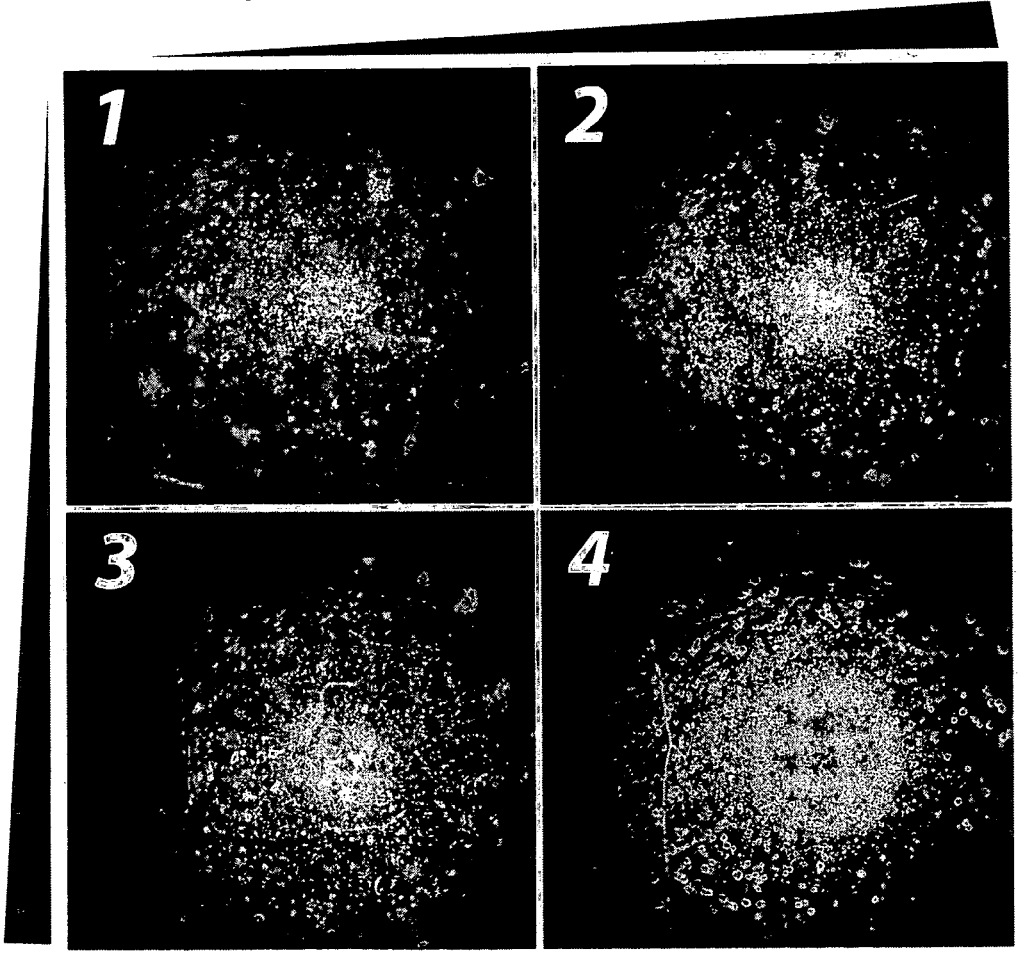
Figure 3:
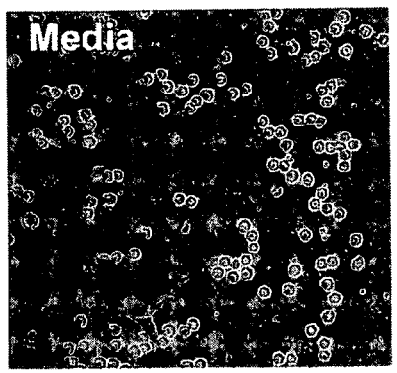
Figure 3:
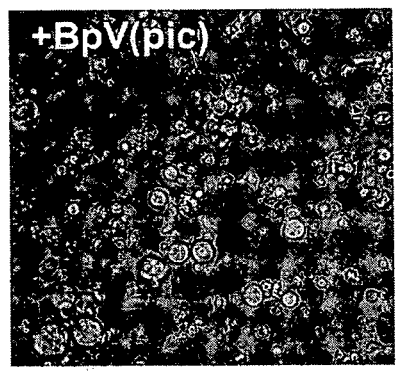
Figure 3:
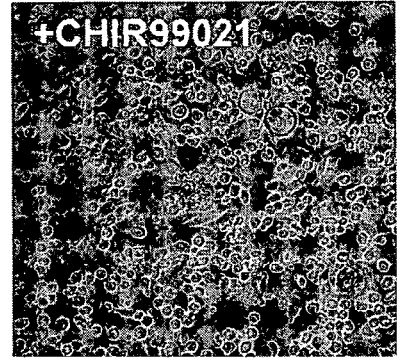
Figure 3:
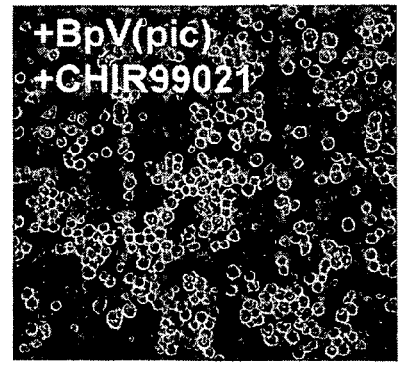
Figure 3:
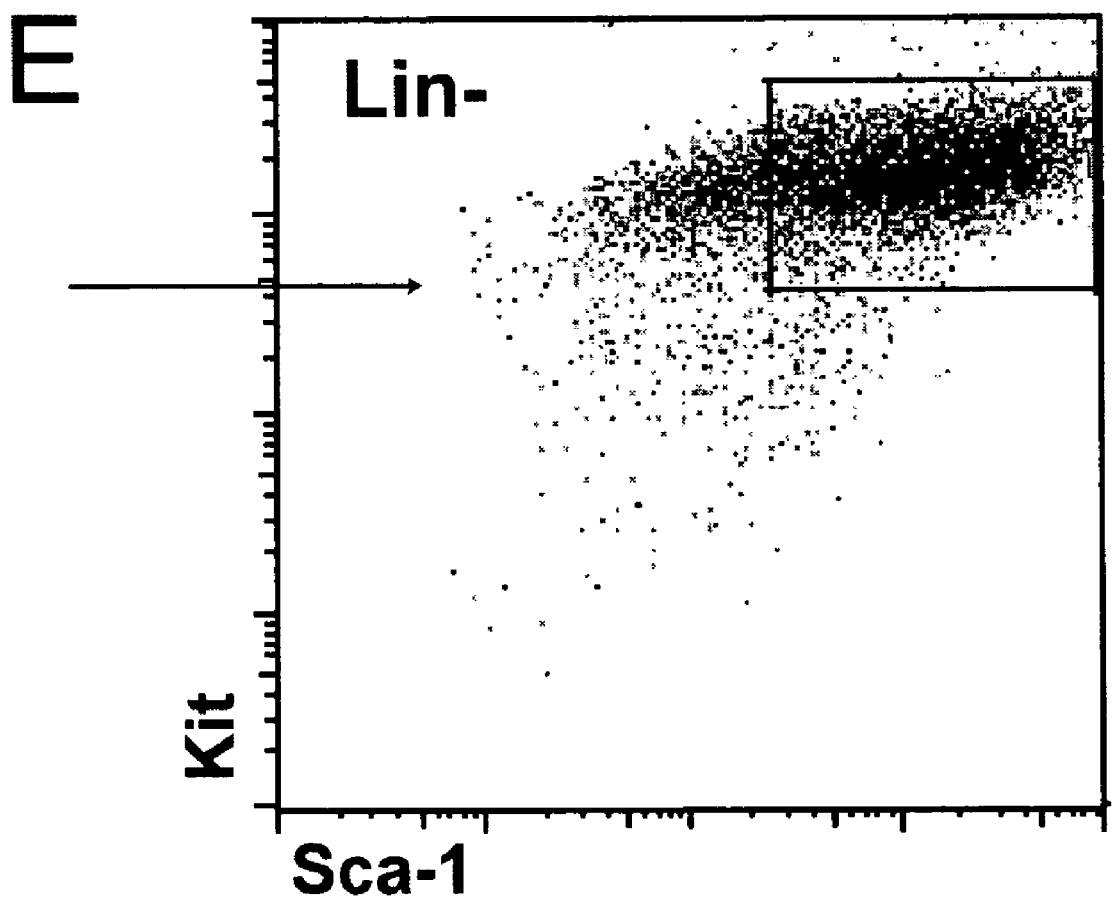
Figure 3:
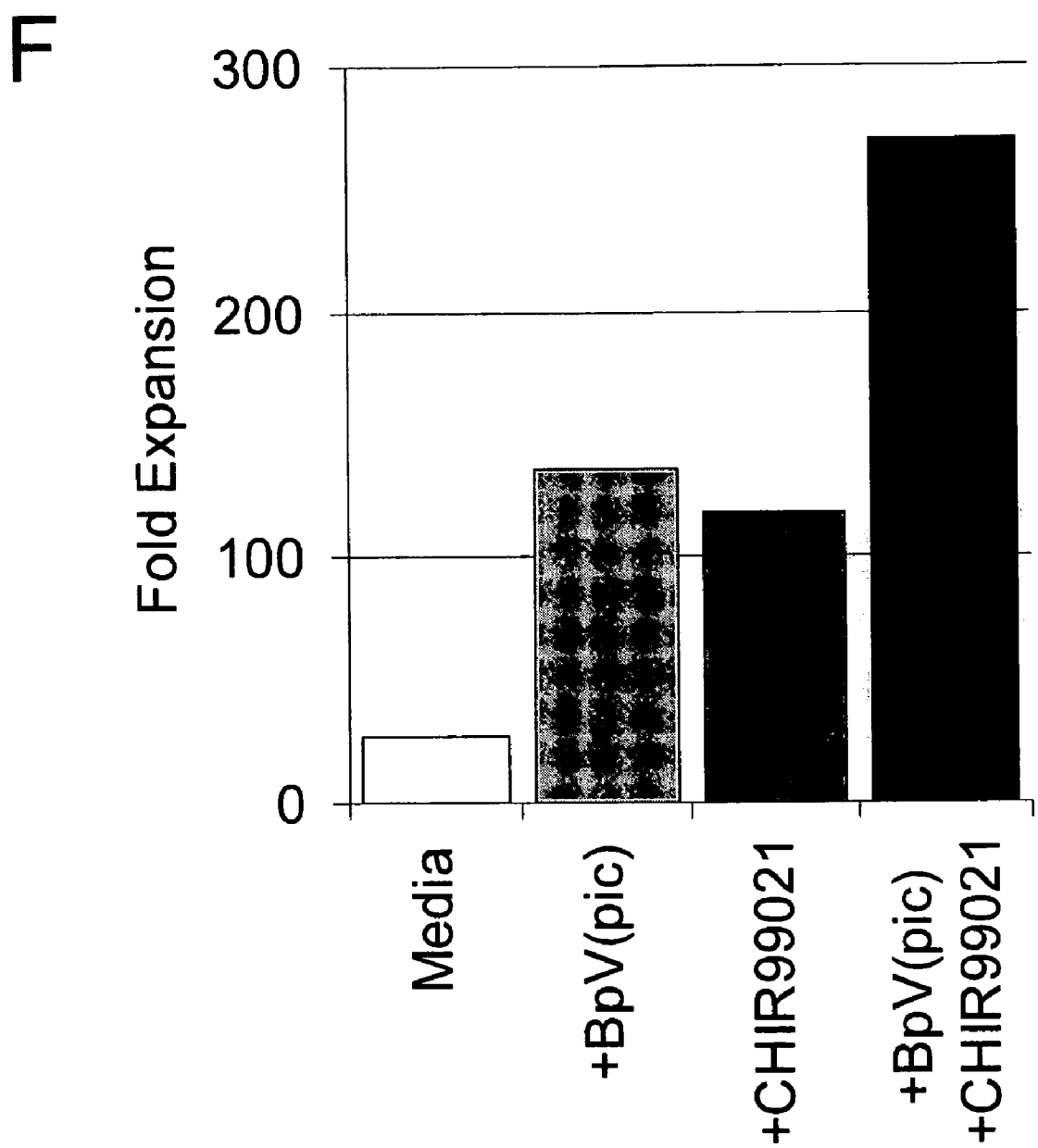
Figure 3:
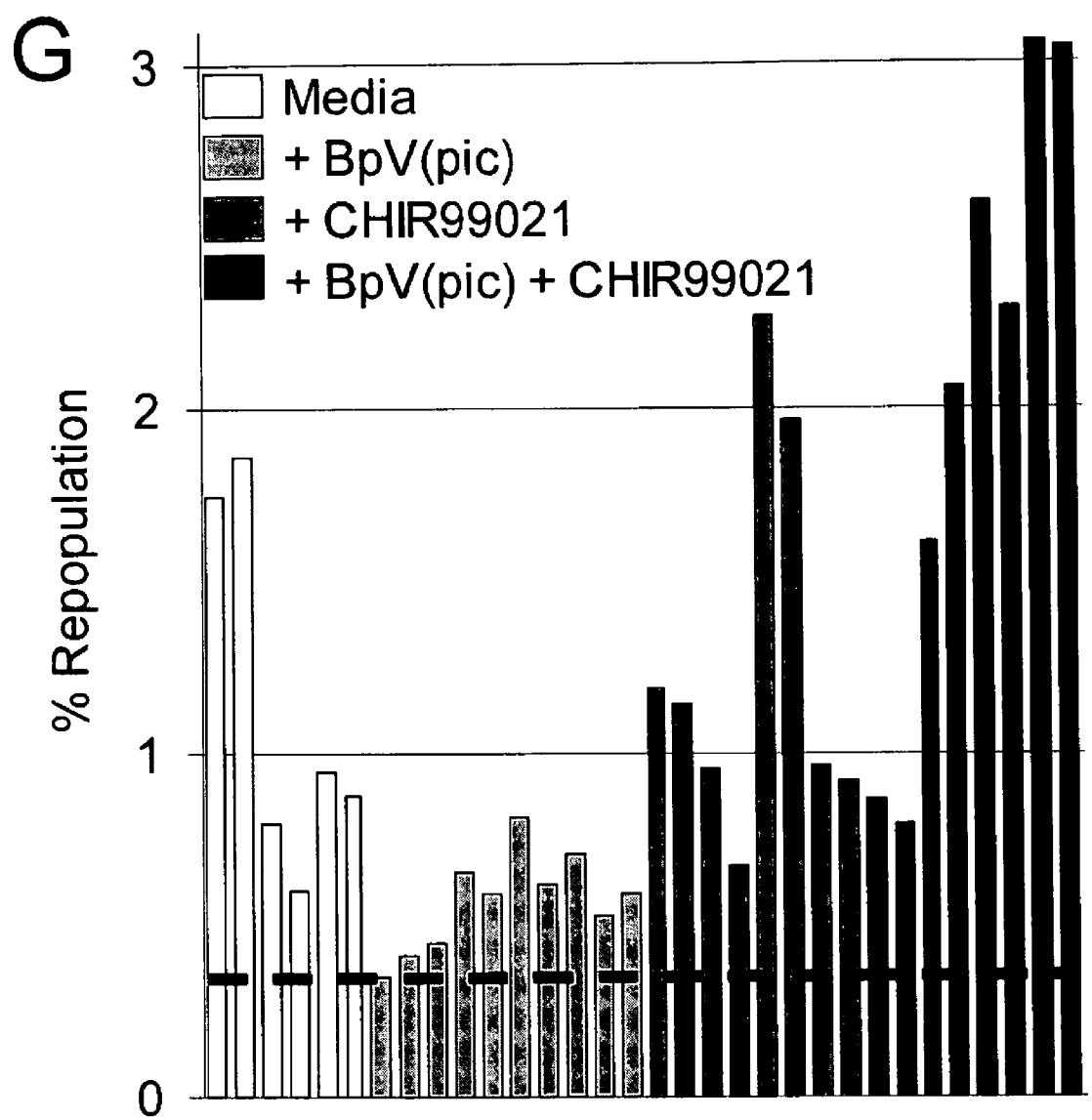
Figure 3:
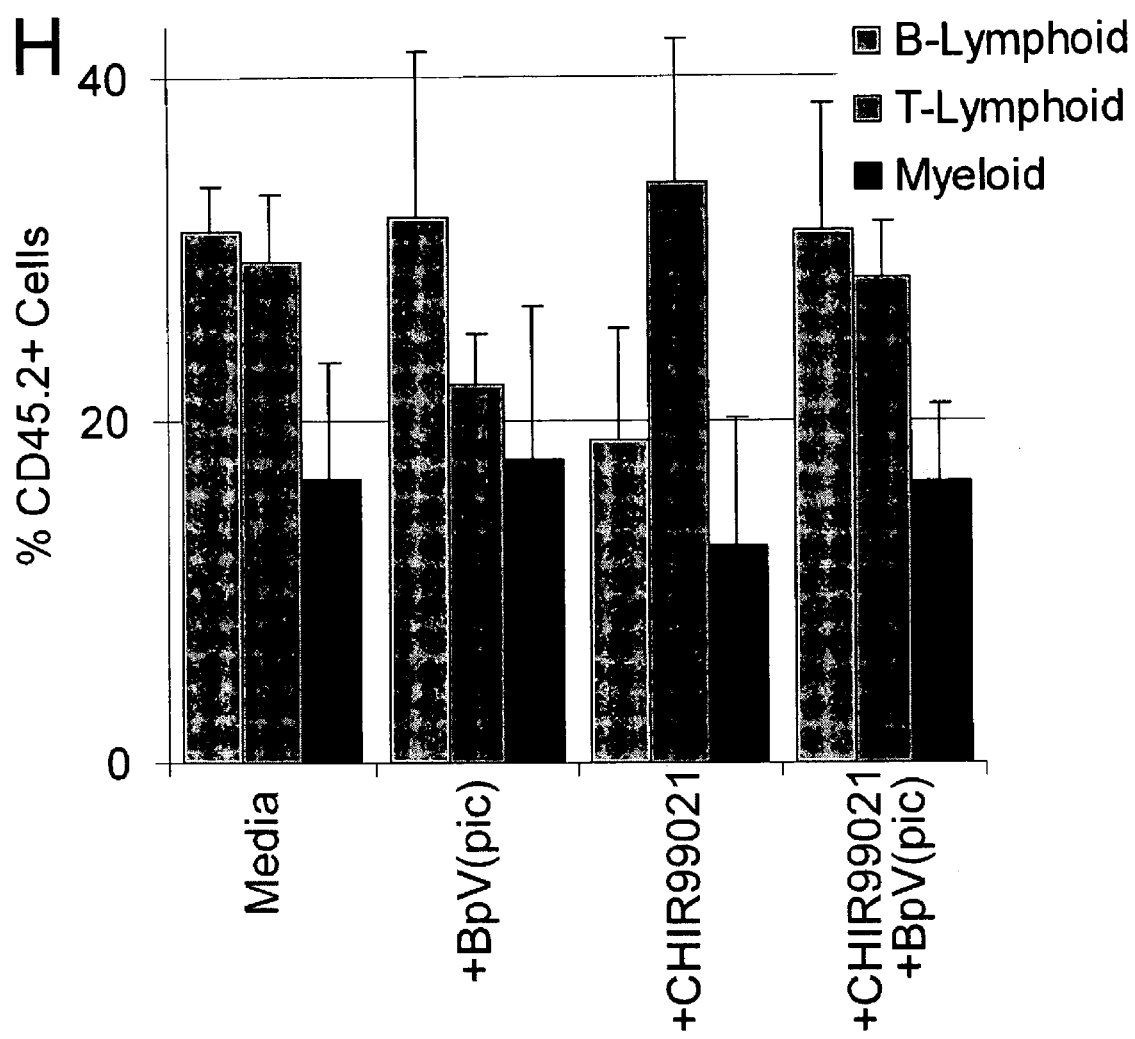
Figure 3:
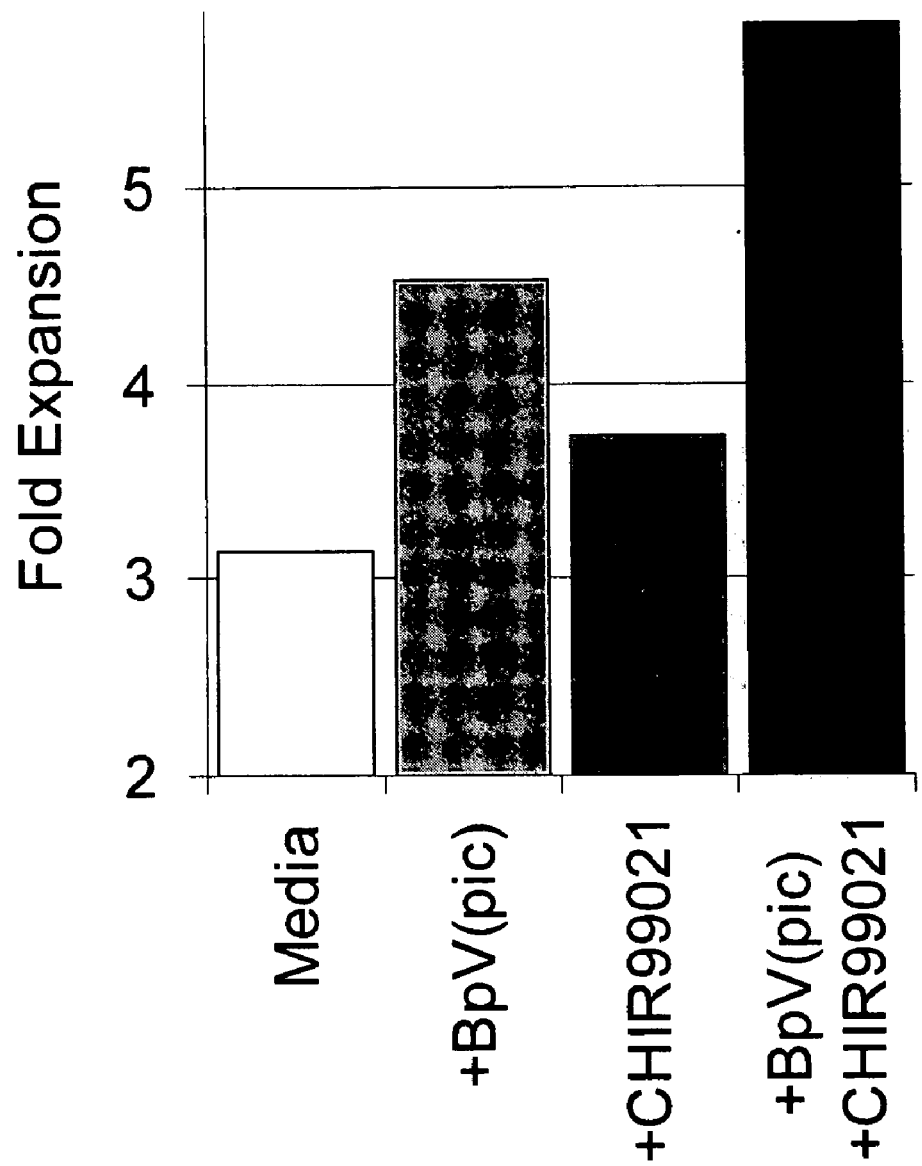
Figure 3:
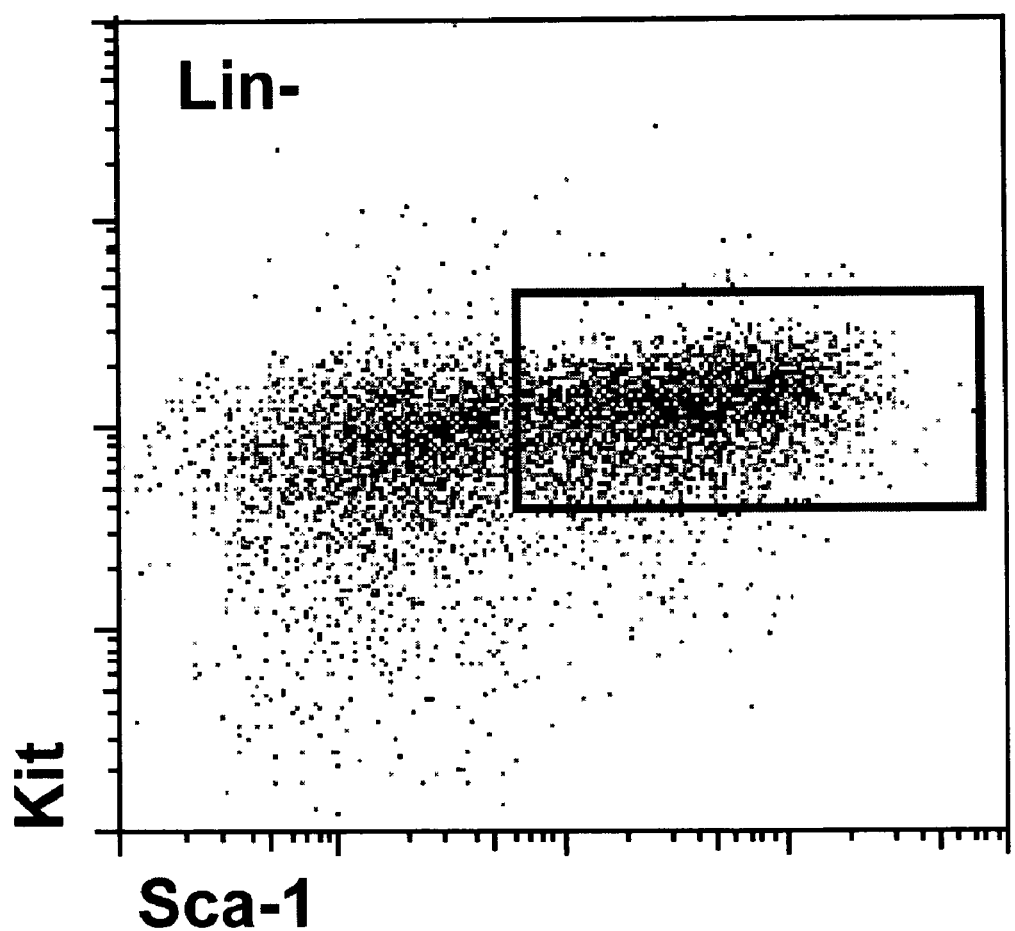
Figure 3:
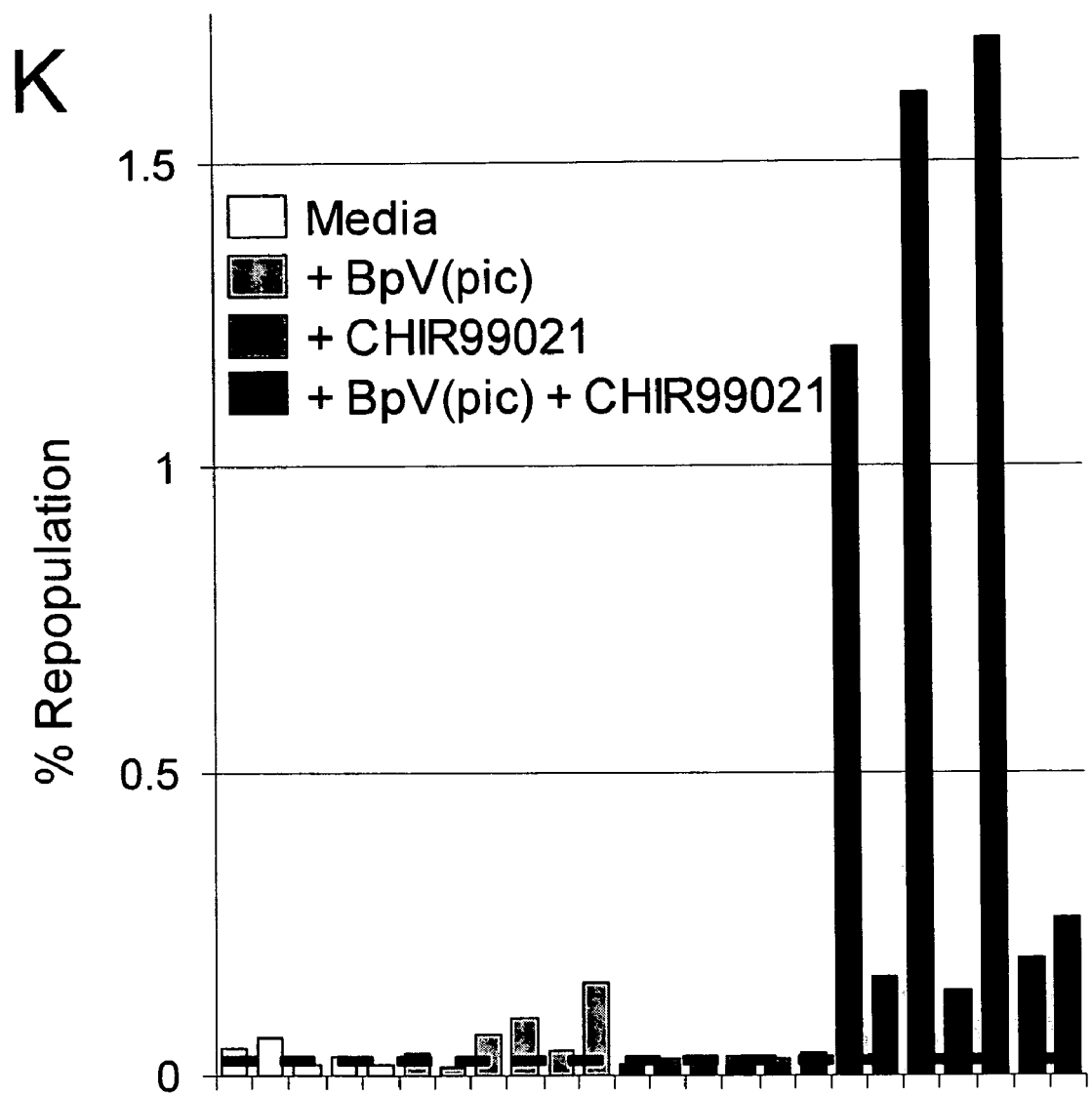

As used herein, "a modulator of a PTEN pathway" (or "PTEN pathway modulator") is any agent that regulates the activity of any member of the PTEN pathway, which results in, e.g., increased β-catenin expression in a stem cell, and/or increased β-catenin function in a stem cell, and/or increased β-catenin localization to a nucleus of a stem cell and/or provides a survival signal complementary to β-catenin. Thus, a modulator of the PTEN pathway may act upstream or downstream of PTEN; preferably the modulator acts at or downstream from PTEN. Inhibition of PTEN leads to Akt activation which promotes survival (FIG. 3A). Representative, non-limiting examples of members of the PTEN pathway, include PTEN, phosphatidylinositol 3-kinase (PI3K), the serine/threonine protein kinase Akt, and β-catenin.

Representative non-limiting examples of PI3K modulators, particularly PI3K activators, include pervanadate (Maude Tessier and James R. Woodgett, J. Biol. Chem., 281 (33):23978-23989 (2006)), insulin (Hui, L., et al., Brain Research, 1052 (1):1-9 (2005)), insulin-like growth factor (Kenney, A. M., et al., Development, 131:217-228 (2004) and Datta, S. R., et al., Cell, 91:231-241 (1997)), platelet derived growth factor (Datta, S. R., et al., Cell 91:231-241 (1997)), carbachol (Cui, Q L, et al., Neurochem Int, 48:383-393 (2006)), nicotine (West, K. et al., J. Clinical Investigation, 111:81-90 (2003)), 4-(methylnitrosamino)-1-(3-pyridyl)-1-butanone (NNK) (Id.), adrenomedullin (AM) (Nikitenko, LL et al., British J. Cancer, 94:1-7 (2006)), lysophosphatidic acid, platelet activating factor, macrophage simulating factor, and sphingosine-1-phosphate.

Representative non-limiting examples of Akt modulators, particularly Akt activators, include Ro-31-8220 (Wen, H. et al., Cellular signaling, 15:37-45 (2003)); Nicotine (West, K. et al., J. Clinical Investigation, 111:81-90 (2003)); carbachol (Cui Q L, Fogle E & Almazan G Neurochem Int, 48:383-393 (2006)); 4-(methylnitrosamino)-1-(3-pyridyl)-1-butanone (NNK) (West, K. et al., J. Clinical Investigation, 111:81-90 (2003)); adrenomedullin (AM) (Nikitenko, L L et al, British J. Cancer, 94:1-7 (2006)); lysophosphatidic acid; platelet activating factor, macrophage simulating factor; sphingosine-1-phosphate; cAMP-elevating agents, such as forskolin, chlorophenylthio-cAMP, prostaglandin-E1, and 8-bromo-cAMP (Song et al., J. Cell. Mol. Med., 9 (1):59-71 (2005)); and growth factors, including insulin and insulin growth factor-1 (Datta, S. R., et al., Cell, 91:231-241 (1997)), and platelet derived growth factor.

Additional preferred modulators of the present invention include those that target mTOR, RHEB, FoxO, p27, BAD, caspase-9, or p53. Representative non-limiting examples of such modulators include mTOR modulators, particularly mTOR activators, such as phosphatidic acid (PA) (see, e.g., WO/2006/027545; Foster, D. A., Cancer Res, 67 (1):1-4 (2007); and Tee et al., J. Biol. Chem. 278:37288-96 (2003)); RHEB modulators, particularly RHEB-GTPase inhibitors, such as RHEB antibodies (see, e.g., WO/2004/048536);

FoxO modulators, particularly FoxO inhibitors, such as FKH (DBD), which is a truncated version of FKHRL1 (see, e.g., Gilley, J., et al., J. Cell Biol. 162 (4):613-622 (2003)); p27 modulators, particularly p27 inhibitors, such as p27 antisense inhibitors and triplex forming oligonucleotides, protein and peptide antagonists (see, e.g., U.S. Pat. No. 5,958,769); BAD modulators, particularly BAD inhibitors, such as 14-3-3 protein (see, e.g., S. Hsu et al., Molecular Endocrinology 11 (12):1858-1867 (1997)); caspase-9 modulators, particularly caspase-9 inhibitors, such as LB-84451 (LG Life Sciences) and Z-LEHD-FMK Caspase Inhibitor (Thornberry, N. A., and Lazebnik, Y., Science 281:1312-1316 (1998)); and p53 modulators, particularly p53 inhibitors, such as Pifithrin-α and its derivatives (see, e.g., Science, Komarov et al., 285 (5434): 1733-1737 (1999), Pietrancosta et al., Drug Dev Res 65:43-49 (2005)).

In the present invention, "a modulator of a Wnt Pathway" (or "Wnt pathway modulator") is any agent that regulates the activity of any member of the Wnt pathway, which results in, e.g., increased β-catenin expression in a stem cell, and/or increased β-catenin function in a stem cell, and/or increased β-catenin localization to a nucleus of a stem cell. A modulator of the Wnt pathway may act upstream or downstream of Wnt. Preferably, the modulator acts at or downstream from GSK-3β. Representative, non-limiting examples of members of a Wnt pathway, include Wnt, seven-transmembrane Frizzled (Fz), the single-pass, LDL receptor-related proteins (LRP) 5/6, Axin, Dishevelled, glycogen synthase kinase 3 beta (GSK-3β), adenomatous polyposis coli (APC), and β-catenin. Inhibition of GSK-3β leads to Akt activation which promotes survival (FIG. 3A).

In one aspect of the present invention, modulating the PTEN pathway comprises introducing a mutation into a population of stem cells, which mutation results in modulation of a molecule in the PTEN pathway. In the present invention, modulation of the PTEN pathway also includes contacting the stem cells with a modulator of a molecule in the PTEN pathway that leads to β-catenin activation. Representative, non-limiting examples of such modulators include a small molecule, a biologic, an antisense RNA, a small interfering RNA (siRNA), and combinations thereof. This aspect of the invention further includes modulating the Wnt pathway, which comprises introducing a mutation into a population of stem cells that results in modulation of a molecule in the Wnt pathway. In the present invention modulation of the Wnt pathway also includes contacting the stem cells with a modulator of a molecule in the Wnt pathway. Representative, non-limiting examples of such a modulator include a small molecule, a biologic, an antisense RNA, a small interfering RNA (siRNA), and combinations thereof.

As used herein, "introducing a mutation" means any conventional method for producing an alteration in the genetic makeup of the stem cell population. Non-limiting examples for introducing a mutation into a stem cell population include mutagenesis via ultra-violet light irradiation, chemical mutagenesis, targeted mutagenesis such as site directed mutagenesis of a stem cell, and creation of a transgenic mouse.

In the present invention, the phrase "modulation of a molecule in the PTEN pathway" means altering the function of a member of the PTEN pathway, which altered function has an effect similar to inhibiting or decreasing the function of PTEN. Non-limiting examples of such "modulation" include constitutively activating β-catenin, constitutively activating Akt, or loss-of-function or null alleles of PTEN. The phrase "modulation of a molecule in the Wnt pathway" means blocking or decreasing the function of a member of the Wnt pathway, which has an effect similar to blocking or decreasing GSK-3β function. Non-limiting examples of such modulation include constitutively activating β-catenin and loss-of-function or null alleles of GSK-3β.

"Modulators of a molecule in the PTEN pathway" are molecules that cause, directly or indirectly, activation of β-catenin. Non-limiting examples of such molecules include those that activate β-catenin, activate Akt, activate PI3K, or inhibit PTEN. "Modulators of a molecule in the Wnt pathway" are molecules that directly or indirectly block or decrease the function of a member of the Wnt pathway. Non-limiting examples of such molecules include those that activate β-catenin or that inhibit GSK-3β, Axin, or APC.

In the present invention, the term "small molecule" includes any chemical or other moiety, other than polypeptides and nucleic acids, that can act to affect biological processes, particularly to modulate members of the Wnt and PTEN pathways. Small molecules can include any number of therapeutic agents presently known and used, or that can be synthesized in a library of such molecules for the purpose of screening for biological function(s). Small molecules are distinguished from macromolecules by size. The small molecules of the present invention usually have a molecular weight less than about 5,000 daltons (Da), preferably less than about 2,500 Da, more preferably less than 1,000 Da, most preferably less than about 500 Da.

Small molecules include without limitation organic compounds, peptidomimetics and conjugates thereof. As used herein, the term "organic compound" refers to any carbon-based compound other than macromolecules such as nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds.

Preferred small molecules are relatively easier and less expensively manufactured, formulated or otherwise prepared. Preferred small molecules are stable under a variety of storage conditions. Preferred small molecules may be placed in tight association with macromolecules to form molecules that are biologically active and that have improved pharmaceutical properties. Improved pharmaceutical properties include changes in circulation time, distribution, metabolism, modification, excretion, secretion, elimination, and stability that are favorable to the desired biological activity. Improved pharmaceutical properties include changes in the toxicological and efficacy characteristics of the chemical entity.

In general, a polypeptide mimetic ("peptidomimetic") is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides, and peptoids.

As used herein, the term "biologic" means products derived from living sources as opposed to a chemical process.

Non-limiting examples of a "biologic" include proteins, conditioned media, and partially purified products from tissues.

The terms "peptide," "polypeptide," and "protein" are used interchangeably herein. In the present invention, these terms mean a linked sequence of amino acids, which may be natural, synthetic, or a modification or combination of natural and synthetic. The term includes antibodies, antibody mimetics, domain antibodies, lipocalins, and targeted proteases. The term also includes vaccines containing a peptide or peptide fragment intended to raise antibodies against the peptide or peptide fragment.

"Antibody" as used herein includes an antibody of classes IgG, IgM, IgA, IgD, or IgE, or fragments or derivatives thereof, including Fab, F(ab')2, Fd, and single chain antibodies, diabodies, bispecific antibodies, and bifunctional antibodies. The antibody may be a monoclonal antibody, polyclonal antibody, affinity purified antibody, or mixtures thereof, which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety. The antibody may be a human or humanized antibody. These and other antibodies are disclosed in U.S. Published Patent Application No. 20070065447.

Other antibody-like molecules are also within the scope of the present invention. Such antibody-like molecules include, e.g., receptor traps (such as entanercept), antibody mimetics (such as adnectins, fibronectin based "addressable" therapeutic binding molecules from, e.g., Compound Therapeutics, Inc.), domain antibodies (the smallest functional fragment of a naturally occurring single-domain antibody (such as, e.g., nanobodies; see, e.g., Cortez-Retamozo et al., Cancer Res. 2004 Apr. 15; 64 (8):2853-7)).

Suitable antibody mimetics generally can be used as surrogates for the antibodies and antibody fragments described herein. Such antibody mimetics may be associated with advantageous properties (e.g., they may be water soluble, resistant to proteolysis, and/or be nonimmunogenic). For example, peptides comprising a synthetic beta-loop structure that mimics the second complementarity-determining region (CDR) of monoclonal antibodies have been proposed and generated. See, e.g., Saragovi et al., Science. Aug. 16, 1991; 253 (5021):792-5. Peptide antibody mimetics also have been generated by use of peptide mapping to determine "active" antigen recognition residues, molecular modeling, and a molecular dynamics trajectory analysis, so as to design a peptide mimic containing antigen contact residues from multiple CDRs. See, e.g., Cassett et al., Biochem Biophys Res Commun. Jul. 18, 2003; 307 (1):198-205. Additional discussion of related principles, methods, etc., that may be applicable in the context of this invention are provided in, e.g., Fassina, Immunomethods. October 1994; 5 (2):121-9.

As used herein, "peptide" includes targeted proteases, which are capable of, e.g., substrate-targeted inhibition of post-translational modification such as disclosed in, e.g., U.S. Patent Application Publication No. 20060275823.

"Antisense" molecules as used herein include antisense or sense oligonucleotides comprising a single-stranded nucleic acid sequence (either RNA or DNA) capable of binding to target mRNA (sense) or DNA (antisense) sequences. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

Antisense molecules can be modified or unmodified RNA, DNA, or mixed polymer oligonucleotides. These molecules function by specifically binding to matching sequences resulting in inhibition of peptide synthesis (Wu-Pong, November 1994, BioPharm, 20-33) either by steric blocking or by activating an RNase H enzyme. Antisense molecules can also alter protein synthesis by interfering with RNA processing or transport from the nucleus into the cytoplasm (Mukhopadhyay & Roth, 1996, Crit. Rev. in Oncogenesis 7, 151-190). In addition, binding of single stranded DNA to RNA can result in nuclease-mediated degradation of the heteroduplex (Wu-Pong, supra). Backbone modified DNA chemistry, which have thus far been shown to act as substrates for RNase H are phosphorothioates, phosphorodithioates, borontrifluoridates, and 2'-arabino and 2'-fluoro arabino-containing oligonucleotides.

Antisense molecules may be introduced into a cell containing the target nucleotide sequence by formation of a conjugate with a ligand binding molecule, as described, e.g., in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described, e.g., in WO 90/10448.

The term small interfering RNA ("siRNA") refers to small inhibitory RNA duplexes that induce the RNA interference (RNAi) pathway. (Elbashir, S. M. et al. Nature 411:494-498 (2001); Caplen, N. J. et al. Proc. Natl. Acad. Sci. USA 98:9742-9747 (2001); Harborth, J. et al. J Cell Sci. 114:4557-4565 (2001).) These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region. As used herein, siRNA molecules are not limited to RNA molecules but further encompass chemically modified nucleotides and non-nucleotides. siRNA gene-targeting may be carried out by transient siRNA transfer into cells (achieved by such classic methods as liposome-mediated transfection, electroporation, or microinjection).

In another aspect of the present invention, modulating the PTEN and Wnt pathways comprises contacting the stem cell population with a small molecule inhibitor of the PTEN pathway and a small molecule inhibitor of the Wnt pathway. Preferably, modulating the PTEN and Wnt pathways comprises down-regulating PTEN and GSK-3β, respectively. As used herein, "down-regulating" means inhibiting or reducing the amount of or inhibiting or decreasing the activity of PTEN and GSK-3β. Such down-regulation may be accomplished using, e.g. antisense RNA, siRNA, antibodies, or small molecules.

Preferably, down-regulating PTEN and GSK-3β comprises contacting the stem cell population with: (a) a reversible PTEN inhibitor selected from the group consisting of a small molecule, a biologic, an antisense RNA, a small interfering RNA (siRNA), and combinations thereof and (b) a reversible GSK-3β inhibitor selected from the group consisting of a small molecule, a biologic, an antisense RNA, a small interfering RNA (siRNA), and combinations thereof. As used herein, "reversible" means that the effect of the down-regulation is not permanent. In the present invention, genetic alteration of both the PTEN and the Wnt pathways leads to an increased ability to self-renew both in vitro as well as in vivo following long-term culture but a failure to differentiate and thus a failure to repopulate the hematopoietic system of transplant recipients. In contrast, use of reversible down-regulators of both pathways, such as, e.g., bpV(pic) and CHIR99201, allows for expansion of functional HSCs, but (1) once the down-regulator is withdrawn, cultured HSCs can differentiate unlike cultured HSCs from genetic mutants, and (2) if such cultured HSC are transplanted, recipient animals do not develop leukemia as genetic mutants do.

Preferably, both the reversible PTEN inhibitor and the reversible GSK-3β inhibitor are small molecules. In one aspect, the reversible PTEN inhibitor is any molecule, such as a small molecule, which is capable of inhibiting PTEN or a down-stream member of the PTEN pathway, which inhibition leads to β-catenin activation. Preferably, the PTEN inhibitor is selected from the group consisting of shikonin, a bisperoxovanadium compound, SF-1751 (Semafore Pharmaceuticals), pharmaceutical salts thereof, and combinations thereof. In this aspect, the bisperoxovanadium compound is selected from the group consisting of bpV(phen)2, bpV(pic), pharmaceutical salts thereof, and combinations thereof.

In the present invention, the reversible GSK-3β inhibitor is any molecule that is capable of reversibly inhibiting GSK-3β. Preferably, such an inhibitor is selected from the group consisting of Hymenialdisine, Flavopiridol, Kenpaullone, Alsterpaullone, Azakenpaullone, Indirubin-30-oxime, 6-Bromoindirubin-30-oxime (BIO), 6-Bromoindirubin-30-acetoxime, Aloisine A, Aloisine B, TDZD8, Compound 12, CHIR98014, CHIR99021 (CT99021), CT20026, Compound 1, SU9516, ARA014418, Staurosporine, Compound 5a, Compound 29, Compound 46, GF109203x (bisindolylmaleimide I), Ro318220 (bisindolylmaleimide IX), SB216763, SB415286, I5, CGP60474, Compound 8b, TWS119, Compound 1A, Compound 17, Lithium, Beryllium, Zinc, small molecule GSK-3β inhibitors (Vertex Pharmaceuticals), NP-12 (Neuropharma), GSK-3β inhibitors (Amphora), GSK-3β inhibitors (CrystalGenomics), SAR-502250 (Sanofi-Aventis), 3544 (Hoffmann-La Roche), GSK-3β inhibitors (Lundbeck), TDZD-8 (Cancer Center, University of Rochester), pharmaceutically acceptable salts thereof, and combinations thereof.

While the PTEN and GSK-3β inhibitors may be contacted with the stem cell population in any convenient manner that achieves the desired level of stem cell expansion, it is preferred that the inhibitors are co-administered. Moreover, multiple GSK-3β and PTEN inhibitors may be contacted with the stem cells. Furthermore, the PTEN and GSK-3β inhibitors may be contacted/administered to the stem cells in concert with other agents suitable for promoting stem cell self renewal. Preferably, the PTEN inhibitor is bpV(pic) and the GSK-3β inhibitor is CHIR99201.

In an additional aspect of the present invention, the number of stem cells is increased by a factor of at least 40-fold. Preferably, the number of stem cells is increased by a factor of at least 80-fold, such as at least 100-fold, including at least 150-fold, at least 200-fold, at least 250-fold, or at least 270-fold. Surprisingly and unexpectedly such levels of stem cell expansion are achieved using the methods of the present invention.

As noted above, the methods of the present invention may be used to expand any population of stem cells. Preferably, the stem cells that may be expanded according to the methods of the present invention may selected from hematopoietic stem cells (HSCs), endothelial progenitor cells (EPCs), mesenchymal stem cells (MSCs), cardiac stem cells (CSCs), neuronal stem cells (NSCs), and combinations thereof. More preferably, the stem cells are HSCs.

Another embodiment of the invention is a method for ex vivo expansion of a substantially undifferentiated stem cell population. This method comprises modulating a PTEN pathway and a Wnt pathway in the undifferentiated stem cell population to expand the number of undifferentiated stem cells without significant differentiation of the stem cell population.

In this embodiment, a stem cell population is "substantially undifferentiated" if a sufficient number of cells in that population retain the ability to self-renew and can give rise to various differentiated cell types when transplanted into a recipient, for example, in the case of an HSC population, repopulating the HSC lineage when transplanted. As used herein, "without significant differentiation" means the expanded stem cell population has a sufficient number of cells that maintain a multi-lineage differentiation potential that the full scope of a target stem lineage may be regenerated upon transplantation of the expanded stem cell population into a recipient. Thus, e.g., in the case of an HSC population, the expanded HSC population, when transplanted into a recipient, is capable of regenerating the entire hematopoietic cell lineage.

A further embodiment of the invention is a method for ex vivo expansion of an hematopoietic stem cell (HSC) population obtained from a tissue selected from the group consisting of peripheral blood, cord blood, and bone marrow. This method comprises modulating a PTEN pathway and a Wnt pathway in the HSC population to expand the HSC population to a sufficient quantity while maintaining a multilineage differentiation potential in the HSC population, which is sufficient for subsequent transplantation into a patient in need thereof.

As used herein, "obtained" from a tissue means any conventional method of harvesting or partitioning tissue from a donor. For example, the tissue may obtained from a blood sample, such as a peripheral or cord blood sample, or harvested from bone marrow. Methods for obtaining such samples are well known to the artisan. In the present invention, the samples may be fresh, i.e., obtained from the donor without freezing. Moreover, the samples may be further manipulated to remove extraneous or unwanted components prior to expansion. The samples may also be obtained from a preserved stock. For example, in the case of peripheral or cord blood, the samples may be withdrawn from a cryogenically or otherwise preserved bank of such blood. Such samples may be obtained from any suitable donor. Preferably, the donor is a mammal, for example, a primate, such as a human. Furthermore, the sample may be obtained from an autologous or allogeneic donor or source. Preferably, the sample is obtained from an autologous source.

In this method, "maintaining a multilineage differentiation potential" means that the expanded HSC population has the ability, when transplanted into a patient in need of such a transplant, to regenerate all the types of progenitor cells e.g., CMP, GMP, MEP, and CLP, and ultimately all the types of blood cells including, e.g., red blood cells, B lymphocytes, T lymphocytes, natural killer cells, neutrophils, basophils, eosinophils, monocytes, macrophages, and platelets in the hematopoietic system.

In the present invention, that quantity of expanded HSCs, which is "sufficient for subsequent transplantation" generally corresponds to that number of HSCs, which would result in greater than about 1% engraftment after transplantation. This is one accepted measure of a successful transplant. In the present invention, any conventional method may be used to determine the % engraftment, including the one set forth in the Examples. Such a measure may be carried out with or without competitor cells, typically and preferably, without competitor cells. (Zhang, C. C., et al., *Nat Med,* 12 (2): 240-5, 2006. Zhang, C. C. and H. F. Lodish, *Blood,* 105 (11): 4314-20, 2005).

In the above described ex vivo expansion methods, modulating the PTEN and Wnt pathways may be achieved as previously set forth. Modulating the PTEN and Wnt pathways may include contacting the stem cell population with a small molecule inhibitor of the PTEN pathway and a small molecule inhibitor of the Wnt pathway. Modulating the PTEN and Wnt pathways may include down-regulating PTEN and GSK-3β, respectively. Preferably, down-regulating the PTEN and Wnt pathways comprises contacting the stem cell population with a reversible PTEN inhibitor and a reversible GSK-3β inhibitor as previously described. Preferably, both the reversible PTEN inhibitor and the reversible GSK-3β inhibitor are small molecules.

The reversible PTEN inhibitor may be selected from the group consisting of shikonin, a bisperoxovanadium compound, SF-1751 (Semafore Pharmaceuticals), pharmaceutical salts thereof, and combinations thereof. Preferably, the bisperoxovanadium compound is selected from the group consisting of bpV(phen)2, bpV(pic), pharmaceutical salts thereof, and combinations thereof.

The reversible GSK-3β inhibitor may be selected from the group consisting of Hymenialdisine, Flavopiridol, Kenpaullone, Aisterpaullone, Azakenpaullone, Indirubin-30-oxime, 6-Bromoindirubin-30-oxime (BIO), 6-Bromoindirubin-30-acetoxime, Aloisine A, Aloisine B, TDZD8, Compound 12, CHIR98014, CHIR99021 (CT99021), CT20026, Compound 1, SU9516, ARA014418, Staurosporine, Compound 5a, Compound 29, Compound 46, GF109203x (bisindolylmaleimide I), Ro318220 (bisindolylmaleimide IX), SB216763, SB415286, I5, CGP60474, Compound 8b, TWS119, Compound 1A, Compound 17, Lithium, Beryllium, Zinc, small molecule GSK-3β inhibitors (Vertex Pharmaceuticals), NP-12 (Neuropharma), GSK-3β inhibitors (Amphora), GSK-3β inhibitors (CrystalGenomics), SAR-502250 (Sanofi-Aventis), 3544 (Hoffmann-La Roche), GSK-3β inhibitors (Lundbeck), TDZD-8 (Cancer Center, University of Rochester), pharmaceutically acceptable salts thereof, and combinations thereof.

In these ex vivo expansion methods, preferably, the PTEN inhibitor is bpV(pic), and the GSK-3β inhibitor is CHIR99201. In these methods, it is preferred that the stem cell is selected from HSCs, endothelial progenitor cells, (EPCs), mesenchymal stem cells (MSCs), cardiac stem cells (CSCs), neuronal stem cells (NSCs), and combinations thereof. Preferably the stem cell is an HSC. In these methods, the HSC is obtained from a mammalian, e.g., primate or human, tissue selected from the group consisting of cord blood, peripheral blood, and bone marrow.

In another aspect of the method for ex vivo expansion of an hematopoietic stem cell (HSC) population, the expansion of the number of stem cells is by at least 40-fold, such as e.g., by at least 80-fold, including at least 100-fold, at least 150-fold, at least 200-fold, at least 250-fold, or at least 270-fold.

Yet another embodiment of the present invention is an expanded, substantially undifferentiated stem cell population made by a method of the present invention, such as, e.g., the method for ex vivo expansion of a substantially undifferentiated stem cell population or the method for ex vivo expansion of an hematopoietic stem cell (HSC) population.

An additional embodiment of the present invention is a method for ex vivo expansion of hematopoietic stem cells (HSCs) by at least 40-fold, wherein the expanded HSCs, are competent to reconstitute an HSC lineage upon transplantation into a mammalian patient in need thereof. This method comprises culturing a population of HSCs in a suitable culture medium comprising a PTEN inhibitor and a GSK-3β inhibitor.

In this aspect of the invention, "competent to reconstitute an HSC lineage" means that the expanded HSCs, when transplanted into a suitable mammalian patient, result in greater than 1% engraftment in the recipient, which engrafted cells are able to differentiate into the cell lineages necessary to have a normal functioning hematopoietic system. In this method, a "suitable culture medium", "fluid media" and "media" which are used interchangeably herein, mean physiologically balanced salt solutions that can maintain a stem cell population for a required period of time, which solution may be supplemented with the PTEN and GSK-3β modulator/inhibitors of the present invention. Such base culture media are well known in the arts. A non-limiting example of a suitable base culture medium for HSCs is StemSpan Media (Stem Cell Technologies; Cat. No. 09600), which is supplemented with 10 ug/ml Heparin, 5× Penicillin/Streptomycin, 10 ng/ml recombinant mouse (rm) Stem Cell Factor, and 20 ng/ml rm-Thrombopoietin.

Typically, the culture media also includes from about 100 to about 1000 nM of the PTEN inhibitor. The culture media may further include from about 50 nM to about 500 nM of the GSK-3β inhibitor. In the present invention, when a range is recited, any value within that range, including the endpoints, is contemplated. Preferably, the culture media includes both the PTEN and the GSK-3β inhibitors at the concentrations indicated. For example, the media may contain as the PTEN inhibitor, bpV(pic), and as the GSK-3β inhibitor, CHIR99201.

In one aspect of this embodiment, the HSCs are obtained from a mammalian tissue, preferably primate or human tissue, which is selected from cord blood, peripheral blood, and bone marrow. In this embodiment, the number of HSCs is expanded by a factor of at least 80-fold, such as at least 100-fold, including at least 150-fold, at least 200-fold, at least 250-fold, or at least 270-fold.

Yet another embodiment of the present invention is a kit for expanding an hematopoietic stem cell (HSC) population for subsequent transplantation into a patient in need thereof. The kit comprises a PTEN inhibitor and a GSK-3β inhibitor as described above and instructions for the use of the inhibitors. Preferably, in the kit, the PTEN inhibitor is bpV(pic) and the GSK-3β inhibitor is CHIR99201. The kit and the components therein may be packaged in any suitable manner for distribution and/or storage.

A further embodiment of the present invention is a media for carrying out ex vivo expansion of a stem cell population. The media comprises a fluid media suitable for maintaining viable stem cells and PTEN and GSK-3β inhibitors present in the media at concentrations sufficient to enable expansion of the stem cell population while maintaining a multilineage differentiation potential in the stem cells.

In this embodiment, a "concentration sufficient to enable expansion" means the minimum concentration of the PTEN and GSK-3β inhibitors, which are sufficient to achieve the desired level of stem cell renewal, e.g., expansion sufficient for successful engraftment.

In one aspect of this embodiment, expansion of the number of stem cells is by a factor selected from the group consisting of at least 40-fold, at least 80-fold, at least 100-fold, at least 150-fold, at least 200-fold, at least 250-fold, or at least 270-fold.

A further embodiment of the present invention is a method for administering an hematopoietic stem cell (HSC) to a patient in need thereof. The method comprises (a) culturing, in a suitable culture media, a sample containing an HSC population in the presence of a modulator of a molecule in the PTEN pathway and a modulator of a molecule in the Wnt pathway for a period of time sufficient to expand the number of HSCs in the sample to a number sufficient to transplant into the patient; (b) removing from the culture the PTEN and Wnt pathway modulators; and (c) administering the HSCs to the patient. In this embodiment, the culture media, sample, and PTEN and GSK-3β modulators are previously described.

An additional embodiment of the present invention is a method for reconstituting bone marrow in a patient in need thereof. The method comprises culturing, in a suitable culture media, a sample containing an HSC population in the presence of a modulator of a molecule in the PTEN pathway and a modulator of a molecule in the Wnt pathway for a period of time sufficient to expand the number of HSCs in the sample to a number that is sufficient to transplant into the patient. Next, the PTEN and Wnt pathway modulators are removed from the culture. Then, the expanded HSCs are administered to the patient in any conventional manner.

In this method, "reconstituting bone marrow" means restoration of all or a portion of the bone marrow in a patient suffering from a disease in which normal bone marrow function has been compromised. Non-limiting examples of such diseases include aplastic anemia, myelodysplastic syndromes (MDS), paroxysmal nocturnal hemoglobinuria (PNH), and blood cancers, such as leukemia. Thus, as used herein, "reconstituted" means that the transplanted HSCs are able to successfully engraft in the host and differentiate into all the cell lineages typically found in or derived from bone marrow.

In this method, "a period of time sufficient to expand the number of HSCs" means the minimum amount of time to expand the HSCs in culture to a point where there is a sufficient number of HSCs for one or more transplantations. Typically, such a period of time may be at least about 10 days in culture. Under certain circumstances, it may be desirable to expand the stem cell, e.g., HSC, population beyond what is required for a single transplantation. For example, it may be desirable to expand the stem cell, e.g., HSC, population to a number sufficient for multiple transplantations, such as e.g., from about 2 to about 100 transplantations. In these circumstances, the excess cells may be preserved for later use by any conventional method, such as e.g., by cryo-preservation.

As indicated previously, "a number sufficient to transplant" means the minimum number of stem cells, e.g., HSCs, necessary to achieve greater than 1% engraftment in a recipient. "Administering the HSCs to the patient" means conventional methods for delivering HSCs to the patient, including but not limited to, delivering the HSCs surgically and/or intravenously. In this embodiment, the tissue the HSCs are obtained from, and the PTEN and GSK-3β inhibitors are as previously described.

An additional embodiment of the present invention is a method for expanding a population of hematopoietic stem cells (HSCs). This method comprises culturing a population of HSCs under conditions sufficient to result in an expansion of the HSC population by at least 40-fold, wherein the expanded population of HSCs is suitable for transplantation into a mammal in need thereof. In this embodiment the "conditions sufficient to result in an expansion of the HSC population" are those conditions that can result in expansion of HSCs in culture by, e.g., at least 40-fold, such as, e.g., by at least 80-fold, at least 150-fold, at least 200-fold, at least 250-fold, or at least 270-fold. "Suitable for transplantation into a mammal" means that the number and quality of HSCs is sufficient to support greater than 1% engraftment in a mammalian recipient, such as, e.g., a primate recipient, including an human recipient, in need thereof.

Yet another embodiment of the present invention is a method for treating a patient in need of a bone marrow transplant, a peripheral blood transplant, or a cord blood transplant comprising administering to the patient a population of HSCs obtained by a method disclosed herein, particularly the methods for expanding a population of hematopoietic stem cells (HSCs).

A further embodiment of the present invention is a method for expanding a population of hematopoietic stem cells (HSCs). The method comprises (a) obtaining from a mammal a tissue sample comprising an HSC population; (b) expanding, in vitro, the HSC population from the sample, wherein (i) the HSC population expands by at least 40-fold; and (ii) the expanded HSC population has the ability to reconstitute an hematopoietic lineage for at least 4-weeks, such as for example at least 8-weeks, after transplantation into a recipient. In this embodiment the "ability to reconstitute an hematopoietic lineage" means that the expanded HSC population when transplanted into a recipient will result in greater than 1% engraftment of HSC in a recipient. In one aspect of this embodiment, the HSC population expands by at least 80-fold, such as e.g., at least 100-fold, including at least 150-fold, at least 200-fold, at least 250-fold, or at least 270-fold. In another aspect of this embodiment, the mammal is a primate, including a human. Preferably, the human requires a peripheral blood transplant, a cord blood transplant, or a bone marrow transplant. In a further aspect, the tissue sample is obtained from a tissue selected from the group consisting of cord blood, peripheral blood, and bone marrow.

An additional embodiment of the present invention is a method for reconstituting an hematopoietic stem cell lineage in a recipient in need thereof. The method comprises (a) obtaining from a mammal a tissue sample comprising an HSC population; (b) expanding, in vitro, the HSC population from the sample, wherein: (i) the HSC population expands by at least 40-fold, such as for example, by at least 80-fold, including at least 100-fold, at least 150-fold, at least 200-fold, at least 250-fold, or at least 270-fold, and (ii) the expanded HSC population has the ability to reconstitute an hematopoietic lineage for at least 4-weeks, for example, at least 8-weeks, after transplantation into a recipient in need thereof; and (c) transplanting the expanded HSC population into a recipient such as a mammal, including a primate or human, in need thereof.

In this embodiment, "reconstituting an hematopoietic stem cell lineage" means that the expanded HSCs, when transplanted into a recipient result in greater than 1% engraftment of hematopoietic cells, which are able to differentiate into the normal hematopoietic lineages. In this embodiment, the human recipient requires a peripheral blood transplant, a cord blood transplant or a bone marrow transplant. Thus, in a further aspect, the tissue sample is obtained from a tissue selected from the group consisting of cord blood, peripheral blood, and bone marrow. The sample may be obtained from an autologous or allogeneic source. Preferably, the sample is obtained from an autologous source.

In the present invention, it is preferred that the expanded HSC population comprises HSCs that have a phenotype selected from the group consisting of $CD34^-$ or $CD34^+/CD38^{-/low}/Thy-1^+/CD90^+/Kit^{-/lo}/Lin^-/CD133^+VEGFR2^+$, which are markers for the most primitive and long-term undifferentiated human HSCs; CD150$^+$/CD48$^-$/CD244$^-$, which is a marker for human HSCs and their progenitors; and/or CD150$^-$/CD48$^-$/CD244$^+$ and CD150$^-$/CD48$^+$/CD244$^+$, which are markers for non-self-renewing multipotent hematopoietic progenitors, and combinations thereof. (See, e.g., Mimeault, M., et al., Stem Cells: A Revolution in Therapeutics—Recent Advances in Stem Cell Biology and Their Therapeutic Applications in Regenerative Medicine and Cancer Therapies. Clin Pharmacol Ther., 82 (3):252-64 (2007)).

The exact proportions of HSCs having these markers in the population is not critical, so long as the expanded HSC population as a whole is sufficient to result in at least 1% engraftment in a recipient.

In another embodiment, the invention is a method for expanding a hematopoietic stem cell population in a mammal in need of such expansion. This method comprises administering to the mammal a therapeutically effective amount of a modulator of Wnt and Akt for a period of time sufficient to expand the HSC population by at least 40-fold with HSCs that possess the ability to reconstitute an hematopoietic lineage in the mammal.

In this method, the respective modulators of Wnt and Akt may be any molecule, such as a small molecule, a biologic, an antisense RNA, a siRNA, or combinations thereof, which acts directly or indirectly to activate β-catenin. Preferably, the Wnt modulator is selected from a Wnt polypeptide, QS11 (Zhang, Q. et al., PNAS, 104 (18):7444-8 (2007)), 2-amino-4-[3,4-(methylenedioxy)benzyl-amino]-6-(3-methoxyphenyl)pyrimidine (Liu, J. et al., Angew Chem Int Ed Engl. 44 (13):1987-90 (2005)), deoxycholic acid (R. Pai et al., Mol Biol Cell. 15 (5):2156-63 (2004)), and combinations thereof. Preferably, the modulator of Akt is selected from the group consisting of Ro-31-8220 (Wen, H. et al., Cellular signaling, 15:37-45 (2003)); Nicotine (West, K. et al., J. Clinical Investigation, 111:81-90 (2003)); carbachol (Cui Q L, Fogle E & Almazan G Neurochem Int, 48:383-393 (2006)); 4-(methylnitrosamino)-1-(3-pyridyl)-1-butanone (NNK) (West, K. et al., J. Clinical Investigation, 111:81-90 (2003)); adrenomedullin (AM) (Nikitenko, L L et al, British J. Cancer, 94:1-7 (2006)); lysophosphatidic acid; platelet activating factor, macrophage simulating factor; sphingosine-1-phosphate; cAMP-elevating agents, such as forskolin, chlorophenylthio-cAMP, prostaglandin-E1, and 8-bromo-cAMP (Song et al., J. Cell. Mol. Med., 9 (1):59-71 (2005)); and growth factors, including insulin and insulin growth factor-1 (Datta, S. R., et al., Cell, 91:231-241 (1997)), platelet derived growth factor, and combinations thereof.

In this method, the Wnt and Akt modulators may be administered using any regimen that effectively expands the HSC population by at least 40-fold with HSCs that possess the ability to reconstitute an hematopoietic lineage in the mammal. Preferably, the Wnt and Akt modulators are co-administered.

In the present invention, a "therapeutically effective amount" is an amount sufficient to effect beneficial or desired results. In terms of treatment of a mammal, a "therapeutically effective amount" of a modulator is an amount sufficient to treat, manage, palliate, ameliorate, or stabilize a condition, such as a bone marrow disease, in the mammal. A therapeutically effective amount can be administered in one or more doses.

The therapeutically effective amount is generally determined by a physician on a case-by-case basis and is within the skill of one in the art. Several factors are typically taken into account when determining an appropriate dosage. These factors include age, sex and weight of the patient, the condition being treated, the severity of the condition and the form of the drug being administered.

Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of animal, and like factors well known in the arts of medicine and veterinary medicine. In general, a suitable dose of a modulator according to the invention will be that amount of the modulator, which is the lowest dose effective to produce the desired effect. The effective dose of a modulator maybe administered as two, three, four, five, six or more sub-doses, administered separately at appropriate intervals throughout the day.

A modulator, particularly a Wnt or Akt modulator of the present invention, may be administered in any desired and effective manner: as pharmaceutical compositions for oral ingestion, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a modulator, particularly a Wnt or Akt modulator, of the present invention may be administered in conjunction with other treatments. A modulator, particularly a Wnt or Akt modulator, of the present invention maybe encapsulated or otherwise protected against gastric or other secretions, if desired.

While it is possible for a modulator, particularly a Wnt or Akt modulator, of the invention to be administered alone, it is preferable to administer the modulator as a pharmaceutical formulation (composition). Such pharmaceutical formulations typically comprise one or more modulators as an active ingredient in admixture with one or more pharmaceutically-acceptable carriers and, optionally, one or more other compounds, drugs, ingredients and/or materials. Regardless of the route of administration selected, the modulator, particularly a Wnt or Akt modulator, of the present invention is formulated into pharmaceutically-acceptable dosage forms by conventional methods known to those of skill in the art. See, e.g., Remington's Pharmaceutical Sciences (Mack Publishing Co., Easton, Pa.).

Pharmaceutically acceptable carriers are well known in the art (see, e.g., Remington's Pharmaceutical Sciences (Mack Publishing Co., Easton, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition comprising a modulator of the invention must be "acceptable" in the sense of being compatible with the other ingredients of the formulation and not injurious to the subject.

Carriers suitable for a selected dosage form and intended route of administration are well known in the art, and acceptable carriers for a chosen dosage form and method of administration can be determined using ordinary skill in the art.

Pharmaceutical compositions comprising a modulator of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active compound may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more modulator in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug containing a modulator of the present invention, it is desirable to slow its absorption from subcutaneous or intramuscular injection. This may be accomplished by the use of a liquid suspension of crystalline or amorphous material having poor water solubility.

The rate of absorption of the drug then depends upon its rate of dissolution which, in turn, may depend upon crystal size and crystalline form. Alternatively, delayed absorption of a parenterally-administered drug may be accomplished by dissolving or suspending the drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The following examples are provided to further illustrate the methods and compositions of the present invention. These examples are illustrative only and are not intended to limit the scope of the invention in any way.

EXAMPLES

Example 1

Loss of PTEN with Constitutively Active β-Catenin Leads to HSC Expansion with Loss of Early Hematopoietic Progenitors Induction of PTEN/Constitutively Active β-Catenin Double Mutant Mice Mice with homozygous floxed (fl) alleles of Pten (Pten$^{fl/fl}$) were bred with Ctnnb1$^{fl/fl}$ mice in which exon 3 of the mouse β-catenin gene (where all phosphorylation target serine/threonine residues are located) was sandwiched by two loxP sequences. (Harada, N., et al., *Embo J*, 18 (21): 5931-42 1999. Yilmaz, O. H., et al., *Nature*, 441:475-82 2006. Zhang, J., et al., *Nature*, 441 (7092): 518-22 2006.) Double heterozygous mice from this cross were then crossed to generate Pten$^{fl/fl}$ Ctnnb1$^{fl/+}$ mice (since Ctnnb1 is a gain-of-function allele, only heterozygous mice for Ctnnb1 are necessary). Concurrently, Pten$^{fl/fl}$ mice were bred with Scl-Cre$^+$ transgenic mice to generate Scl-Cre$^+$ Pten$^{fl/+}$ mice. These were then crossed to generate Scl-Cre+Pten$^{fl/fl}$ mice ("Pten"). Finally, Pten$^{fl/fl}$ Ctnnb1$^{fl/+}$ mice were bred with Scl-Cre$^+$ Pten$^{fl/fl}$ mice to generate Scl-Cre$^+$ Pten$^{fl/fl}$ Ctnnb1$^{fl/+}$ mice ("Pten:Ctnnb1"). Scl-Cre mice were also bred with Ctnnb1$^{fl/fl}$ mice to generate the single mutant Scl-Cre$^+$ Ctnnb1$^{fl/+}$ mice ("Ctnnb1"). Mice lacking Scl-Cre ("Scl-Cre negative" or "Control") were used as controls.

Scl-Cre is an HSC-specific Tamoxifen inducible Cre-recombinase used to achieve conditional knockout of LoxP flanked (floxed) Pten and Ctnnb1 alleles. (Gothert, J. R., et al., "In vivo fate-tracing studies using the Scl stem cell enhancer: embryonic hematopoietic stem cells significantly contribute to adult hematopoiesis." *Blood*, 2005. 105 (7): p. 2724-2732). Pten/constitutively active β-catenin double mutant mice were induced by intra-peritoneal injection of Tamoxifen (Sigma, Cat. No. T5648) everyday for 5 days using 5 mg on day 1 and 2 mg on days 2-5 each dissolved in 0.1 ml of corn oil (Sigma, Cat. No. C8267) (complete dissolution was achieved by 42° C. water bath sonication for about 5 minutes).

HSC Analysis in Bone Marrow and Spleen

Six weeks post-induction of Tamoxifen, bone marrow and spleens were harvested and made into single cell suspensions. Red blood cell lysis was performed using hemolysis buffer (0.16M ammonium chloride, Sigma Cat. No. A9434). Cells were stained for lineage markers using CD3, CD4, CD8, B220, IgM, Mac-1, Gr1, and Ter119 antibodies along with Kit, and Sca-1 for LSK analysis or these markers along with IL-7Rα, CD34 and CD16/32 for progenitor analysis (Akashi, K., et al., *A clonogenic common myeloid progenitor that gives rise to all myeloid lineages*. Nature 2000. 404 (6774): p. 193-7). Flk2 was added as indicated for LT-HSC analysis.

Unless otherwise indicated, all antibodies were obtained from eBiosciences (San Diego, Calif.) as indicated below: Fluorescein isothiocyanate (FITC) conjugated CD3 antibody (Cat. No. 11-0452-85), FITC conjugated CD4 antibody (Cat. No. 11-0042-85), FITC conjugated CD8 antibody (Cat. No. 11-0081-85), FITC conjugated B220 antibody (Cat. No. 11-0452-85), FITC conjugated Ter119 antibody (Cat. No. 11-5921-85), FITC conjugated Mac-1 antibody (Cat. No. 11-0112-85), FITC conjugated Gr1 antibody (Cat. No. 11-5931-85), FITC conjugated IgM antibody (Cat. No. 11-5790-85), Phycoerythrin (PE) conjugated Sca-1 antibody (Cat. No. 12-5981-83), Allophycocyanin (APC) conjugated Kit antibody (Cat. No. 17-1171-83), Biotin conjugated CD135 (Flk-2) antibody (Cat. No. 13-1351-85), PE-Cy5 conjugated CD127 (IL-7Rα) antibody (Cat. No. 15-1271-83), PE-Cy7 conjugated CD16/32 (FcγRII/III) antibody (Cat. No. 25-0161-82), Biotin conjugated CD34 antibody (Cat. No. 13-0341-85), Streptavidin conjugated PE-Cy7 antibody (Cat. No. 25-4317-82), Streptavidin conjugated APC-Cy7 antibody (Cat. No. 10-4317-82), APC conjugated Gr1 antibody (Cat. No. 17-5931-82), APC conjugated B220 antibody (Cat. No. 17-0452-83), PE conjugated Mac-1 antibody (Cat. No. 12-0112-83), and PE conjugated CD3 antibody (Cat. No. 12-0031-85).

Antibody stained cells were sorted by FACS using a MoFlo (Dako, Ft. Collins, Colo.) flow cytometer and/or a CyAn ADP (Dako, Ft. Collins, Colo.), and analyzed for lineage negative, Sca-1$^+$Kit$^+$ (LSK) cells in Scl-Cre negative control and Scl-Cre$^+$ PTEN with constitutively activated β-catenin (Pten:Ctnnb1) double mutant bone marrow and spleen.

Figure 1:
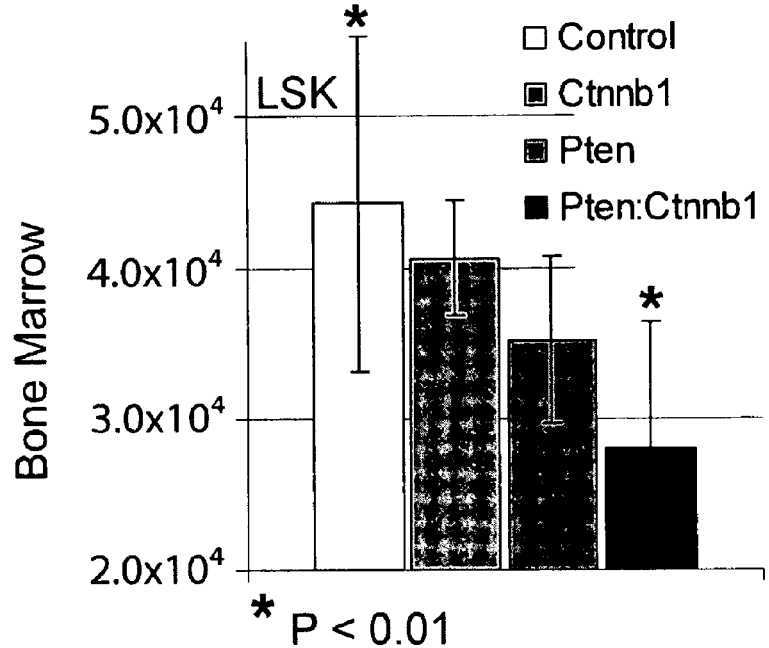
FIGS. 1A-K are a series of bar graphs and fluorescence activated cell scanning ("FACS") analyses that collectively show that loss of PTEN with constitutively active β-catenin leads to hematopoietic stem cell (HSC) expansion with loss of early hematopoietic progenitors.
Figure 1:
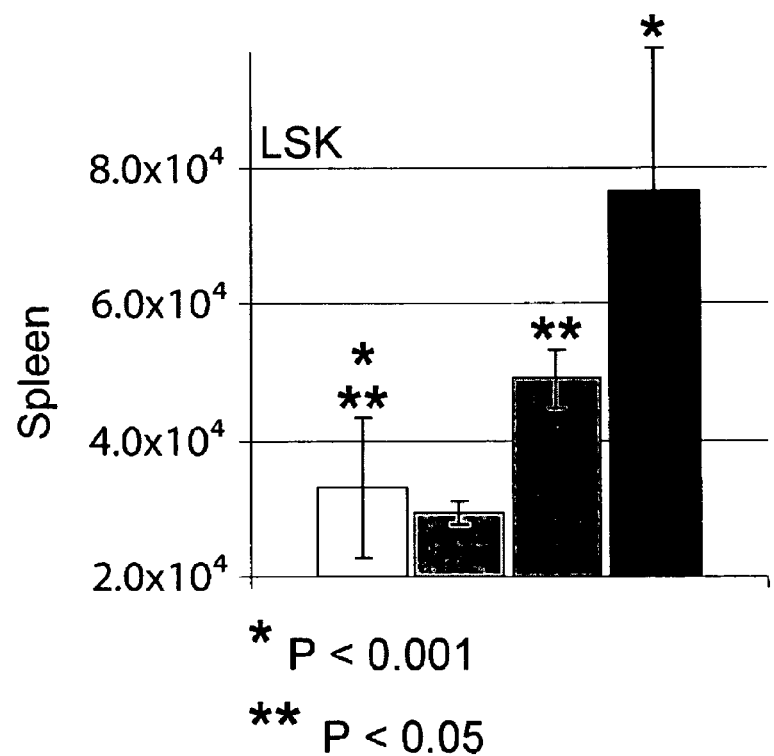
Figure 1:
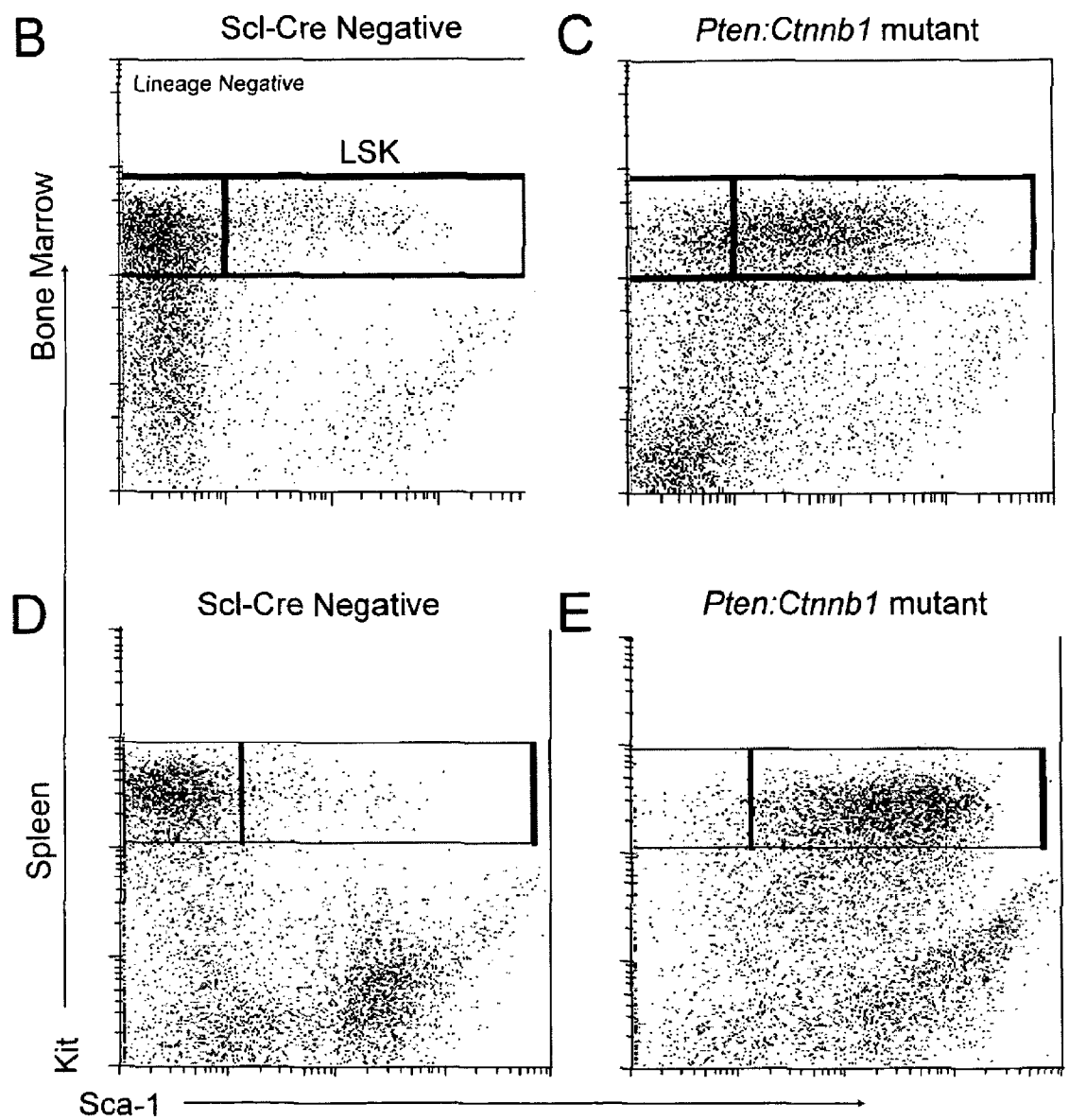
Figure 1:
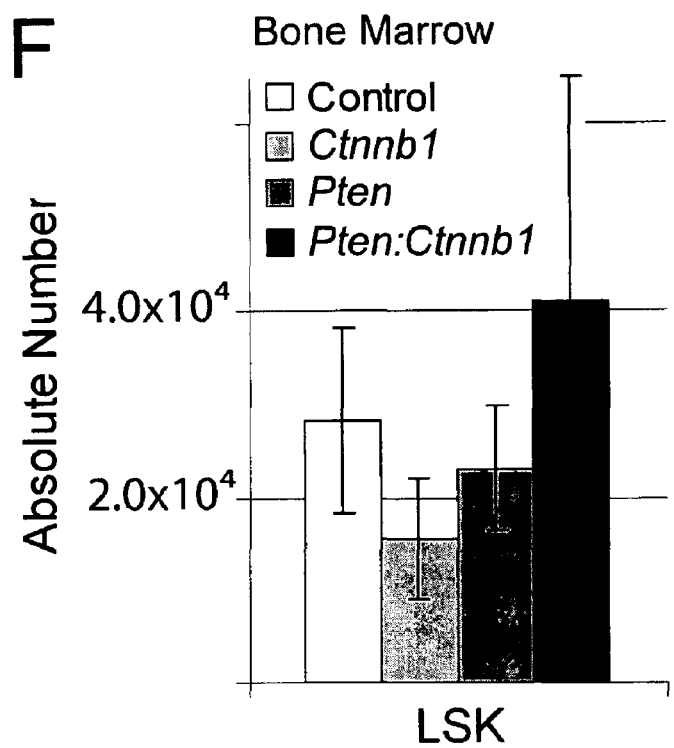
Figure 1:
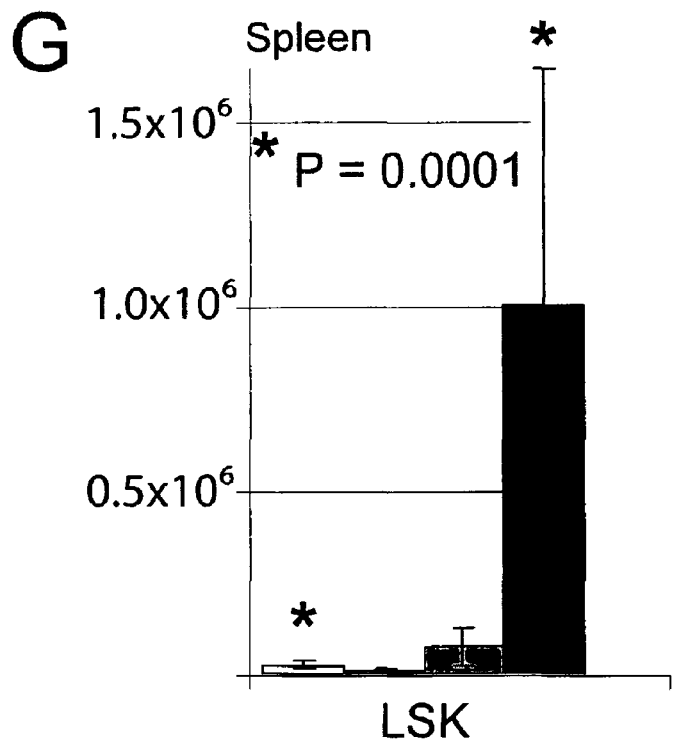
Figure 1:
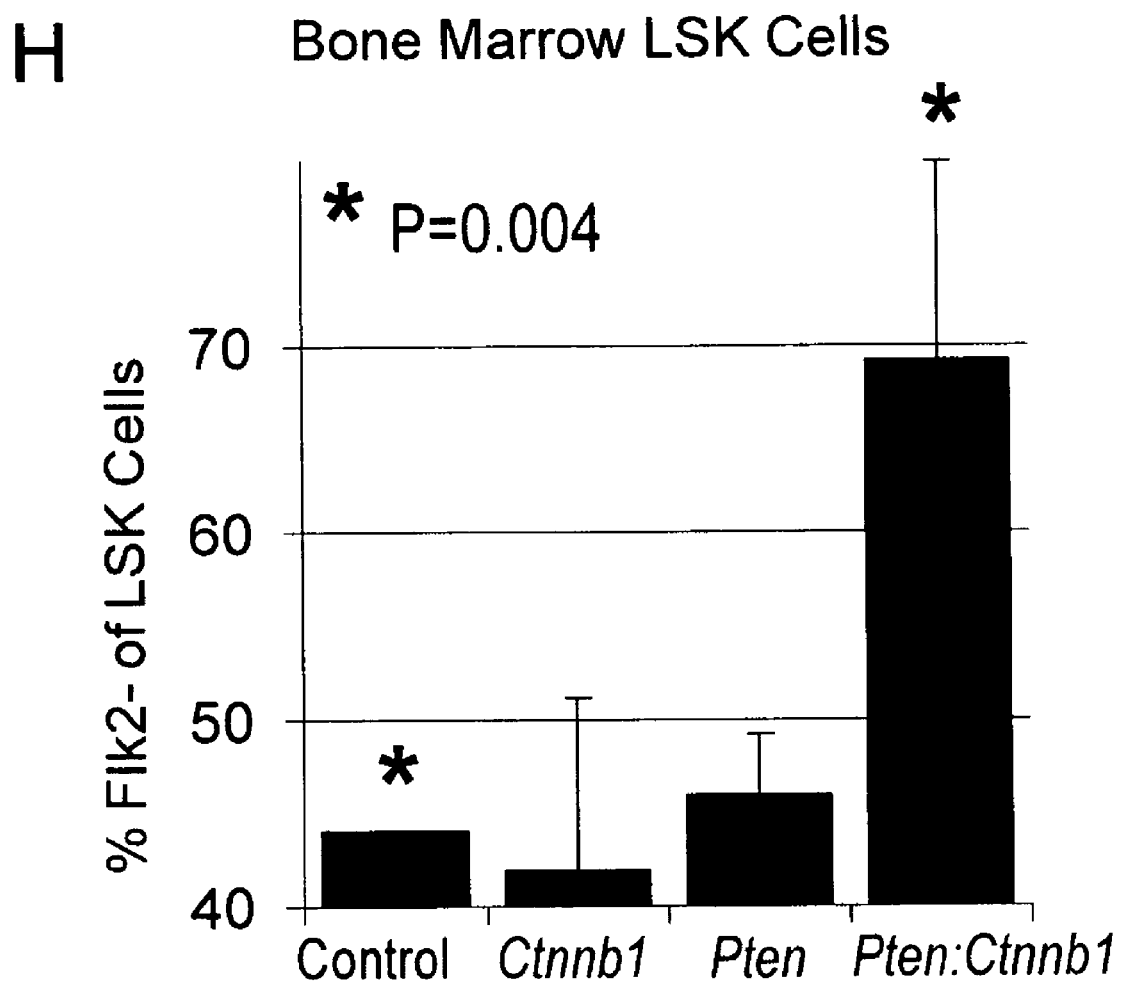
Figure 1:
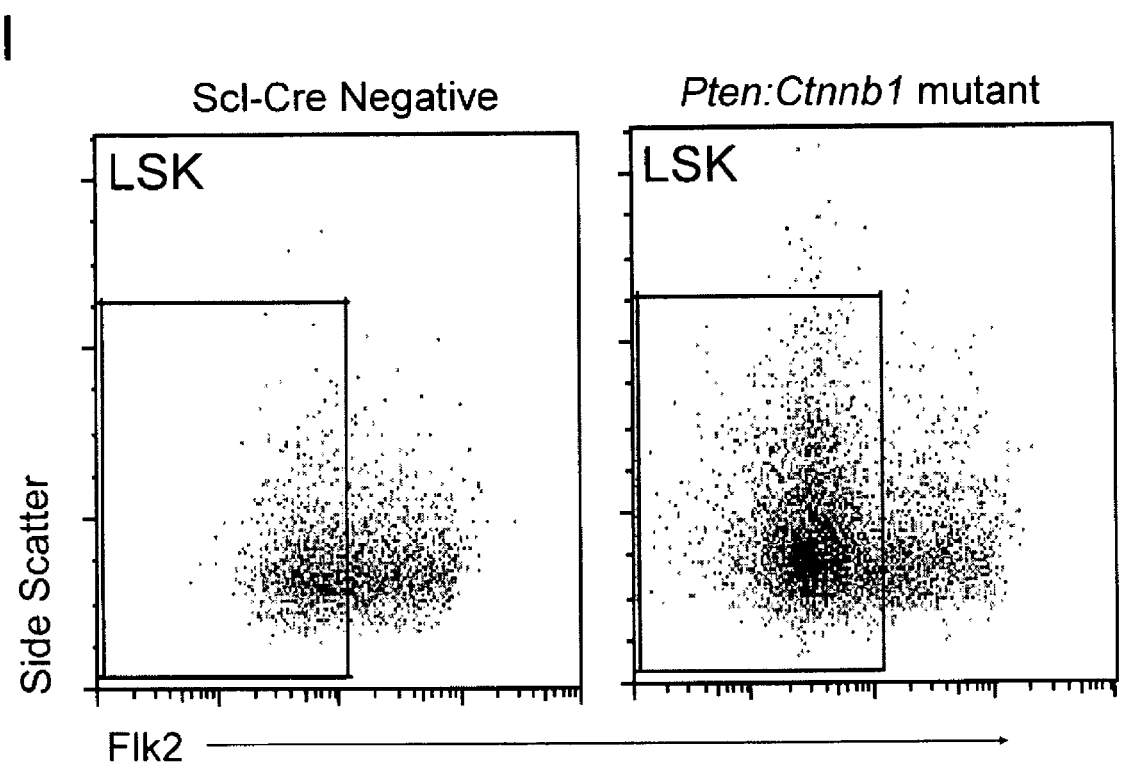
Figure 1:
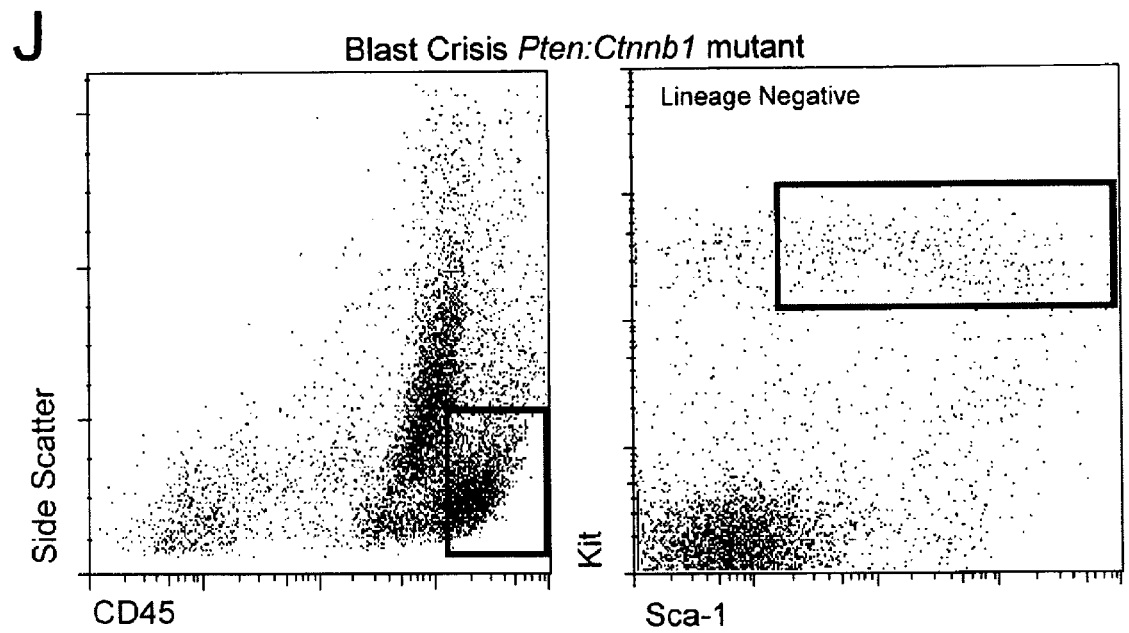
Figure 1:
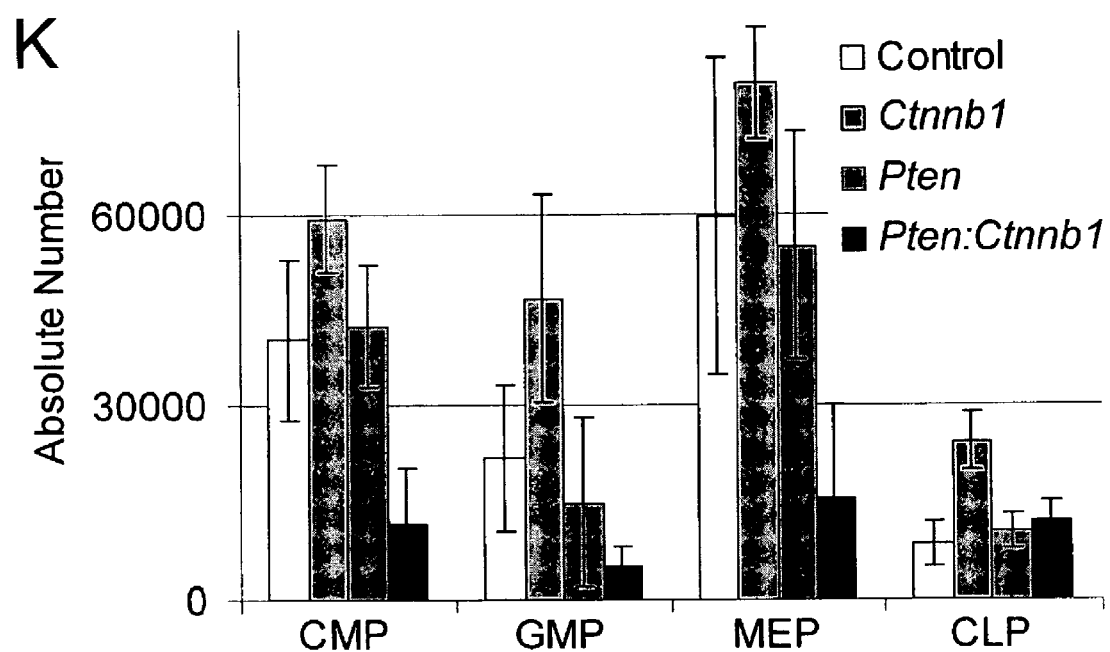

The absolute numbers (per femur+tibia) of lineage negative, Sca-1$^+$Kit$^+$ (LSK) cells in Scl-Cre negative control and Scl-Cre$^+$ PTEN with constitutively activated β-catenin (Pten:Ctnnb1) double mutant and each single mutant bone marrow (FIG. 1A top) and spleen (FIG. 1A bottom) as determined by FACS analysis were counted. (Harada, N., et al., *Embo J*, 18 (21): 5931-42 1999. Yilmaz, O. H., et al., *Nature*, 441:475-82 2006. Zhang, J., et al., *Nature*, 441 (7092): 518-22 2006.) Mice are at 10 days post-induction of Tamoxifen. Reduction of LSK cells in double mutant bone marrow with expansion in the spleen is indicative of mobilization from bone marrow to spleen.

FACS analysis was performed on LSK cells from Scl-Cre negative control and Scl-Cre+ PTEN with constitutively activated β-catenin (Pten:Ctnnb1) double mutant and each single mutant bone marrow and spleen (see FIGS. 1B-E for representative examples of FACS analysis). Cells were pre-gated on live, lineage negative cells.

Absolute number of LSK cells per femur and tibia in control, Pten, and Pten:Ctnnb1 mutant bone marrow (FIG. 1F) and spleen (FIG. 1G) at 6 weeks post-induction were counted. While the percentage of LSKs is increased in double mutants (see FIG. 1C), low cellularity of bone marrow from double mutants yields only moderately increased absolute numbers compared to control.

The percentage of LSK cells which were Flk-2− (indicating long-term reconstituting (LT)-HSCs) in control, Pten, and Pten:Ctnnb1 mutant bone marrow at 6 weeks post-induction were calculated. (FIGS. 1H-I). The percent of LT-HSC cells in Pten:Ctnnb1 double mutant mice were greatly increased in comparison to the control and to Pten single mutant mice. Ctnnb1 single mutants were not significantly different from controls at this time point (data not shown).

FACS analysis of CD45 in leukemic Pten:Ctnnb1 mutant bone marrow was performed. As shown in FIG. 1J, CD45 (high) blast crisis cells are indicated in the blue box of the left panel. In comparison, no blast cell population is observed in control or Ctnnb1 single mutants while a minor one was observed in 1 of 8 Pten single mutant mice at 6 weeks post-induction (data not shown).

LSK analysis of leukemic Pten:Ctnnb1 mutant mouse bone marrow was also performed (FIG. 1J, right panel). Note the conversion to blast cells (lower left) with only a remnant LSK population (compare to FIG. 1C).

Early hematopoietic progenitors were sorted and analyzed by FACS in control, Pten, and Pten:Ctnnb1 mutant bone marrow (FIG. 1K). Absolute numbers of CMPs; GMPs; MEPs; and CLPs were determined.

Together, this data demonstrates the phenotypic effect of the genetic loss of PTEN coupled with constitutive activation of β-catenin in HSCs. While loss of PTEN alone results in a slight but significant expansion in splenic HSCs due to mobilization from the bone marrow, double mutant HSCs exhibit the greatest mobilization at 10 days post-induction. By six weeks post-induction, only double mutant splenic HSCs are dramatically increased while single mutants are not significantly different from controls. In addition, this dramatic increase in HSCs is not accompanied by an increase in early hematopoietic progenitors; rather these early progenitors are all reduced with the exception of CLPs which are not significantly different from control. HSCs accumulate dramatically in the spleen of double, but not single, mutants by proliferation with reduced differentiation. Thus, surprisingly and unexpectedly, loss of PTEN coupled with the constitutive activation of β-catenin drives stem cell self-renewal while neither pathway individually is capable of driving long-term self-renewal.

Example 2

In Vitro Culture of Control and Mutant LSK Cells

Cell Culture

LSK or LSK Flk2− cells were sorted into 96-well U-bottom tissue culture plates at 100 cells/well with 200 µl media/well. Cells were incubated at 37° C., 5% $O_2$, 5% $CO_2$ (balance $N_2$) for the indicated number of days. One-half total volume of media (see Table 1, below for the base media) was carefully pipetted from the top and replaced with fresh media every other day.

TABLE 1

Base Media

| Components | Source |
|---|---|
| StemSpan Media: (Iscove's-modified Dulbecco's medium (IMDM) supplemented with 1% bovine serum albumin, 10 µg $ml^{-1}$ recombinant human insulin, 200 µg $ml^{-1}$ iron-saturated transferrin, 0.1 mM 2-mercaptoethanol and 2 mM glutamine.) | Stem Cell Technologies; Cat. No. 09600 |
| 10 µg/ml Heparin | Sigma, Cat. No. H-3149 |
| 0.5X Penicillin/Streptomycin | Sigma, Cat. No. P4333 |
| 10 ng/ml recombinant mouse (rm) Stem Cell Factor | Biovision, Cat. No. 4328-10 |
| 20 ng/ml rm-Thrombopoietin | Cell Sciences, Inc, Cat. No. CRT401B |

Double Mutant HSCs Expand Dramatically in Vitro and in Vivo but Fail to Differentiate.

For the following experiments, the base media from Table 1 was further supplemented with 20 ng/ml rm-IGF-2 (R&D Systems, Cat. No. 792-MG) and 10 ng/ml recombinant human FGF-1 (Affinity BioReagents, Cat. No. ORP16010).

One hundred LSK cells isolated from control, constitutively active β-catenin (Ctnnb1), Pten mutant, and double mutant (Pten:Ctnnb1) mice were cultured for 10 days (FIG. 2A). Cell numbers were not dramatically increased from the 100 seeded LSKs in control, while Ctnnb1 single mutant LSKs did not survive. In contrast, Pten single mutant LSKs exhibited greater proliferation but appeared more heterogeneous indicating more significant differentiation. The greatest and most homogeneous expansion occurred from Pten:Ctnnb1 double mutant LSKs.

LSK cells isolated from Pten and Pten:Ctnnb1 mutants were examined at 34 days culture (FIG. 2B). Wild-type control cultures did not expand beyond 4 weeks; Ctnnb1 mutant cultures did not survive beyond 10 days. Pten mutant HSC cultures appeared more heterogenous with significant cell clumping and more irregular cell morphology. Also note the spindle-shaped adherent cells (arrows) showing differentiation. In contrast, double mutant HSC cultures exhibited consistent morphology. Therefore, while Pten single mutant LSKs survived and expanded, they had undergone more significant differentiation than the much more homogeneous Pten:Ctnnb1 double mutant LSKs.

At 7 weeks culture, Pten and Pten:Ctnnb1 LSK cultures were counted and analyzed by FACS for maintenance of the LSK phenotype (FIG. 2E). Again, wild-type control and Ctnnb1 cultures did not survive this long in vitro. Double mutant LSKs undergo >1,200 fold expansion compared to 50 fold for Pten single mutant LSKs. LSK purity of cultures was significantly greater in Pten:Ctnnb1 cultures maintaining the LSK phenotype in about 85% of total live cells compared to about 50% for Pten single mutant cultures.

Collectively these data demonstrate that double mutant HSCs can be cultured longer and with far greater expansion than either single mutant or control HSCs.

Example 3

Transplantation Analysis of Pten and Pten:Ctnnb1 LSK Cells after 5 Weeks of Culture For the following experiments, cells were cultured in the same manner as described in Example 2. As in Example 2, the base media of Table 1 was supplemented with 20 ng/ml rm-IGF-2 (R&D Systems, 792-MG) and 10 ng/ml recombinant human FGF-1 (Affinity BioReagents, ORP16010).

At 5 weeks culture, Pten and Pten:Ctnnb1 LSK cultures were re-sorted and 1000 LSK cells (CD45.2$^+$) from each were transplanted into lethally irradiated (10Gy) CD45.1$^+$ recipient mice along with 2×10$^5$ congenic whole bone marrow competitor cells. Because wild-type cells did not survive 5 weeks culture, 1000 fresh wild-type LSK cells were also transplanted as a separate control group. At 4 weeks post-transplant, there was no detectable engraftment from peripheral blood analysis of mice transplanted with either Pten or Pten:Ctnnb1 LSK cultures (data not shown). At 5 weeks post-transplant, bone marrow from recipient mice was analyzed for donor engraftment (CD45.2$^+$ cells) and donor LSK cells (CD45.2$^+$ LSKs).

FIGS. 2F and 2G show representative donor engraftment (left) and donor LSK cell engraftment (right) from bone marrow of mice transplanted with 1000 fresh LSK cells (F) or 1000 cultured Pten:Ctnnb1 LSK cells (G). FIGS. 2H, 2I, and 2J show quantitation of donor (CD45.2$^+$) cells (H), donor LSK cells (I), and fold-increase in donor LSKs (FIG. 2J) isolated from bone marrow of recipient mice described in FIGS. 2F and G at 5 weeks post-transplant. Although the absolute number of Pten:Ctnnb1 donor cells per fermur is lower than that of control or Pten single mutant donor cells, the number of Pten:Ctnnb1 donor LSK cells is significantly higher than either that of control or Pten single mutant donor LSK cells.

Collectively, these data demonstrate that double mutant HSCs can be cultured longer and with far greater expansion than either single mutant or control HSCs. However, permanent genetic alteration of both pathways leads to an increased ability to self-renew both in vitro as well as in vivo following long-term culture but a failure to differentiate and thus repopulate the hematopoietic system of transplant recipients. This further demonstrates the ability of the PTEN and β-catenin signaling pathways to cooperatively drive stem cell expansion by proliferation without differentiation Example 4

Ex Vivo Pharmacological Manipulation of the PTEN/Akt and Wnt/β-Catenin Signaling Pathways Cooperatively Drive Functional HSC Expansion One hundred LSK Flk2$^-$ cells were sorted from wild-type (C57Bl/6) mice and cultured in (1) media, (2) media+1 μM CHIR99021 (a GSK-3β inhibitor, a gift from Dr. Sheng Ding), (3) media+200 nM Dipotassium Bis-peroxo(picolinato)oxovanadate (BpV(pic), a PTEN inhibitor, available from Calbiochem, Cat. No. 203705), (4) media+1 μM CHIR99021+200 nM BpV(pic), (5) media+200 nM Shikonin (also a PTEN inhibitor, available from Calbiochem, Cat. No. 565850), and (6) media+200 nM Shikonin+1 μM CHIR99021. (FIGS. 3B-C). Cells were cultured as described above. Cells were examined at 17 days of culture (FIG. 3B, original magnification 100×) and 23 days (FIG. 3C, original magnification 40×). Compared to control, both inhibitors applied individually exhibited greater expansion of LSK cells indicating that GSK-3β inhibition is not strictly equivalent to constitutive activation of β-catenin shown in Ctnnb1 mutant LSKs, while BpV(pic) exhibited similar results compared to Pten mutant LSKs (see FIG. 2). Similar to double mutant LSKs (FIG. 2), the greatest expansion occurred with both inhibitors present (FIG. 3B/C panel 4).

LSK Flk2$^-$ cells at 28 days culture in the indicated media conditions were examined (FIG. 3D, original magnification 200×). Here, significant expansion relative to control was observed with both inhibitors present individually; however, significant differentiation/heterogeneity of cell morphology was observed in both cases, including more variable cell size/morphology and/or differentiation to adherent, spindle-shaped cells (middle panels). In contrast, expansion with homogeneity was achieved when both inhibitors were present (last panel).

FACS analysis of 28 day LSK Flk2$^-$ cells cultured in media+BpV(pic)+CHIR99021 (FIG. 3E) was performed. Cells were pre-gated on live, lineage negative cells. Greater than 90% of LSKs retained Flk2 negativity (data not shown). Thus, the LSK Flk2$^-$ phenotype was maintained with high purity in cultures containing both inhibitors.

Fold expansion of LSK Flk2$^-$ cells after 28 days culture in (1) media, (2) media+BpV(pic), (3) media+CHIR99021, and (4) media+CHIR99021+BpV(pic) were analyzed. While each inhibitor added individually led to significant expansion compared to media without either inhibitor, the greatest expansion (~270 fold) was observed when both inhibitors were added together.

Collectively, these data demonstrate that the PTEN/Akt and Wnt/β-catenin signaling pathways can be manipulated pharmacologically to drive HSC expansion. The greatest expansion is achieved by manipulating both pathways simultaneously. Functional, short-term HSCs show highest reconstitution ability when cultured in the presence of both inhibitors. Substantial longer-term reconstitution (8 weeks) occurs only when HSCs are cultured in the presence of both inhibitors but not when cultured with either single inhibitor or in the absence of either inhibitor. Thus, the pharmacological manipulation of both pathways simultaneously results in the greatest expansion of functional HSCs.

Example 5

Transplantation Analysis of Cultured LSK Cells after Ex Vivo Pharmacological Manipulation Cell Harvest and Repopulation Cells were harvested from the wells prior to transplantation by pipetting up and down several times before transferring to a fresh tube. Residual was then collected by adding more media and repeating. Cells were washed in DMEM (Invitrogen, Cat. No. 31053) without phenol red and added to the appropriate number of whole bone marrow rescue cells from a congenic donor (for 200,000 rescue cells+1,000 re-sorted LSK Flk2$^-$ cells (FIG. 3F-H) or the non-adherent product of 10 days culture of 100 LSK Flk2$^-$ cultured cells (FIG. 3I-K) per mouse as indicated). Cells were injected into lethally irradiated (10 Grays, single dose) Ptprc (CD45.1$^+$) recipient mice through the tail vein using an insulin syringe.

Repopulation was measured at 4 weeks post-transplant by collection of peripheral blood, red blood cell lysis, and staining of CD45.1 (recipient) compared to CD45.2 (donor) engraftment using antibodies purchased from eBiosciences (FITC conjugated CD45.2 (Cat. No. 11-0454-85) and PE-Cy5 conjugated CD45.1 (Cat. No. 15-0453-82)). Mice transplanted with rescue/competitor cells only were used as a control to determine the limits of repopulation detection. Multi-lineage reconstitution was determined by CD3, B220 (for lymphoid) and Gr1, Mac-1 (for myeloid), as described above.

Transplantation Analysis of 28 Day Cultures.

Cells cultured for 28 days in (1) media, (2) media+BpV (pic), (3) media+CHIR99021 and (4) media+CHIR99021 (1 µM)+BpV(pic) (200 nM) were re-sorted for LSK Flk2⁻ cells. One thousand LSK Flk2⁻ cells (CD45.2⁺) from each media condition were transplanted into lethally irradiated (10Gy) CD45.1⁺ recipient mice along with 2×10⁵ congenic whole bone marrow competitor cells. At 4 weeks post-transplant, peripheral blood was analyzed for donor (FIG. 3G) and multi-lineage (FIG. 3H) engraftment. In FIG. 3G, each bar represents an individual mouse. The horizontal-dashed line represents the average 'engraftment' of mice transplanted with competitor cells only and, thus, the limit of detectability for true engraftment. Long-term (4 month) engraftment has not been observed from 28-day cultures (data not shown). Six of 8 mice show >1% engraftment when transplanted with LSK Flk2⁻ cells cultured with both inhibitors present compared to 4/8 with only CHIR99021 present, 0/10 with only BpV(pic) present, and 2/6 with media only. One percent or greater engraftment is a standard limit for substantial engraftment. (Zhang, C. C., et al., *Nat Med,* 12 (2): 240-5, 2006. Zhang, C. C. and H. F. Lodish, *Blood,* 105 (11): 4314-20, 2005). Thus, while both inhibitors together leads to greatest expansion in LSKs (FIG. 2F), transplantation of equivalent numbers of these cultured LSK Flk2⁻ cells also leads to increased short-term engraftment/functionality when cultured with both inhibitors compared to no or either single inhibitor only.

While all mice with genetic alterations resulting in constitutively active β-catenin and loss of PTEN will develop leukemia and must be sacrificed due to poor health within 8-10 weeks post-mutation induction (FIG. 1I and data not shown), no mice transplanted with LSK Flk2⁻ cells cultured in either inhibitor singly or in combination has shown any sign of leukogenesis up to 16 weeks post-transplantation. All such mice appeared healthy unlike 8-10 weeks post-induction genetically double mutant mice, exhibiting no loss of body weight, anemia, loss of appetite, lethargy, hunched posture, etc. Thus, the effects of the inhibition of both pathways using, e.g., BpV(pic) and CHIR99021, is reversible.

Transplantation Analysis of 10 Day Cultures.

Cells cultured for 9 days in (1) media, (2) media+BpV(pic) (200 nM), (3) media+CHIR99021 (100 nM), and (4) media+CHIR99021 (100 nM)+BpV(pic) (200 nM) were re-sorted for LSK Flk2⁻ cells, and fold expansion of LSK Flk2⁻ cells after 9 days culture in the indicated conditions was determined (FIG. 3I). Because long-term engraftment was not observed from 28 day cultures (FIG. 3D-H and data not shown), LSK Flk2⁻ cells were cultured for only 9 days to test if both expansion and long-term repopulation could be achieved. Similar trends were observed here when compare to the 28 day cultures (compare to FIG. 9F) although the extent of expansion was substantially reduced at only 9 days versus 28 days culture.

FACS analysis was performed on 9 day LSK Flk2⁻ cells cultured in media+BpV(pic) (200 nM)+CHIR99021 (100 nM) (FIG. 3J). Cells were pre-gated on live, lineage negative cells. Greater than 90% of LSKs retain Flk2 negativity (data not shown). Here, the levels of Sca-1 and Kit appear normal compared to the Sca-1$^{(high)}$Kit$^{(high)}$ population shown from 28 day cultures (FIG. 1E).

Ten day cultures were transplanted into lethally irradiated (10Gy) CD45.1⁺ recipient mice along with 2×10⁵ congenic whole bone marrow competitor cells. The total, non-adherent cell product after 10 days culture of 100 initial LSK Flk-2 cells was transplanted per mouse. At 8 weeks post-transplant, peripheral blood was analyzed for donor (FIG. 3G) and multi-lineage (FIG. 3H) engraftment. As shown, multi-lineage reconstitution was observed from all mice exhibiting true engraftment (data not shown). In FIG. 3G, each bar represents an individual mouse; the horizontal-dashed line represents the average 'engraftment' of mice transplanted with competitor cells only and thus the limit of detectability for true engraftment. Here, 3/7 mice transplanted with LSK Flk2⁻ cells cultured in the presence of both inhibitors exhibited 1% or greater donor engraftment compared to no mice reaching this threshold in the single or no inhibitor groups.

Figure 2:
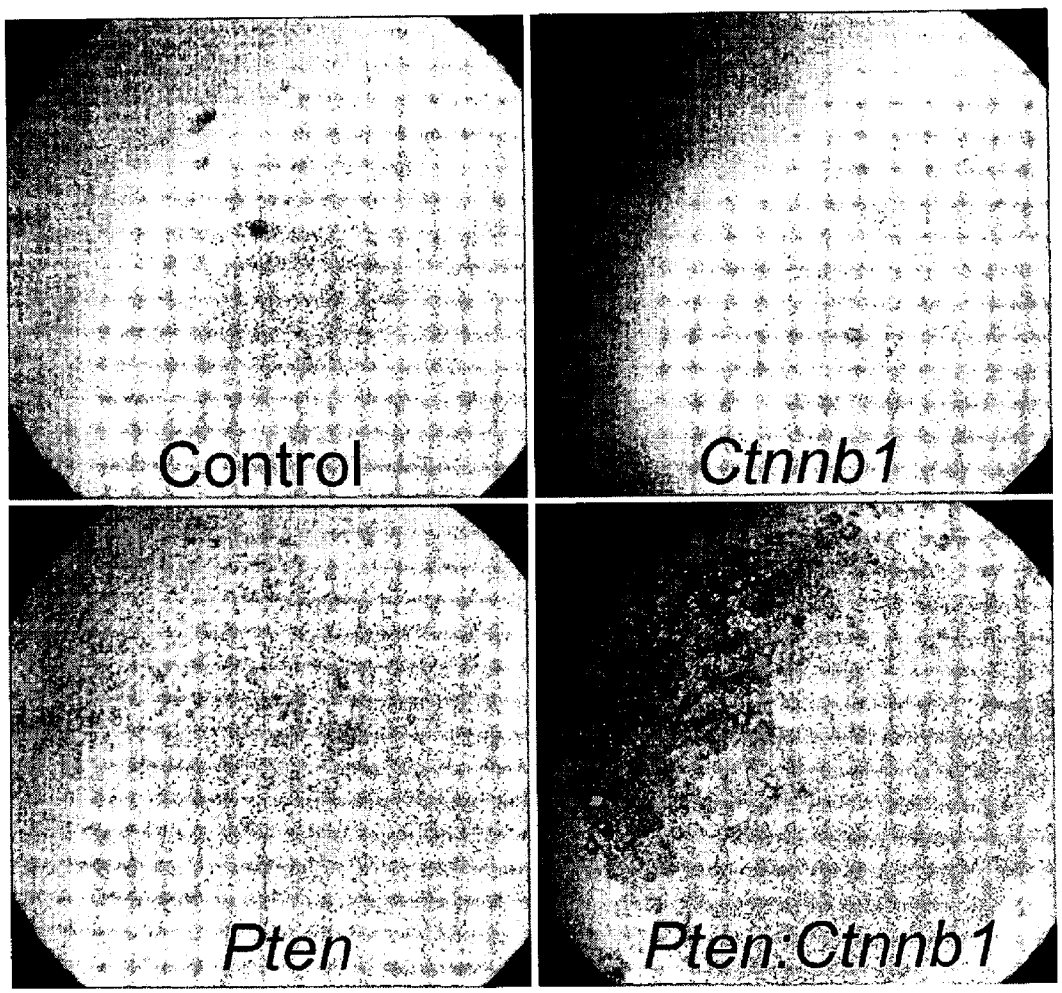
FIGS. 2A-J are a series of photographs, bar graphs, and FACS analyses that collectively show that double mutant HSCs expand dramatically in vitro and in vivo but fail to differentiate.
Figure 2:
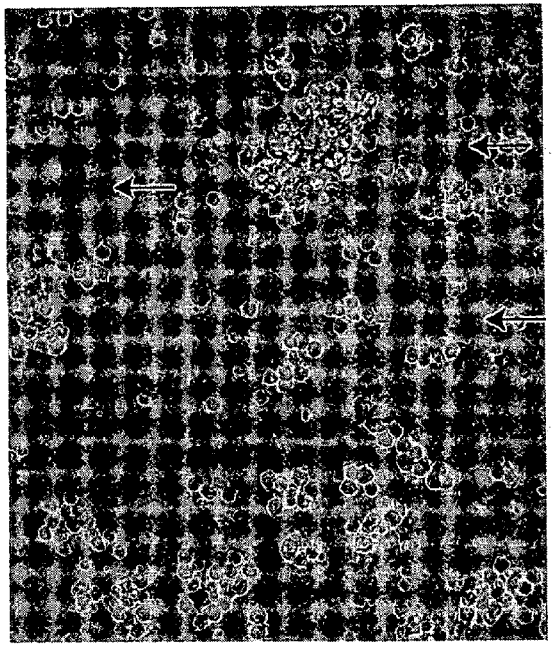
Figure 2:
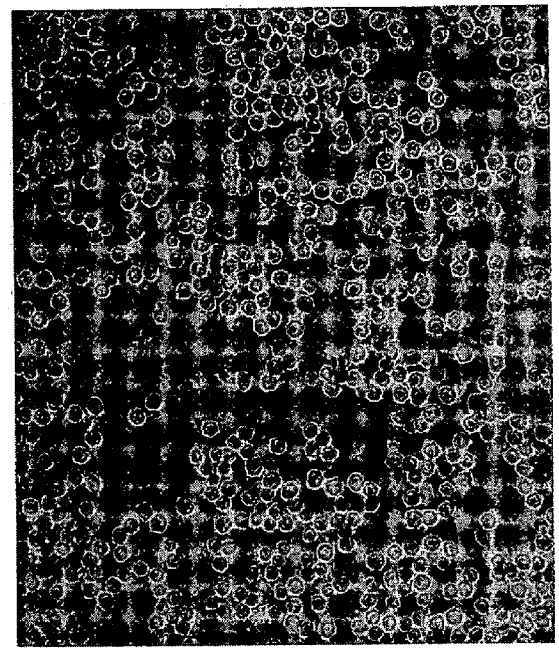
Figure 2:
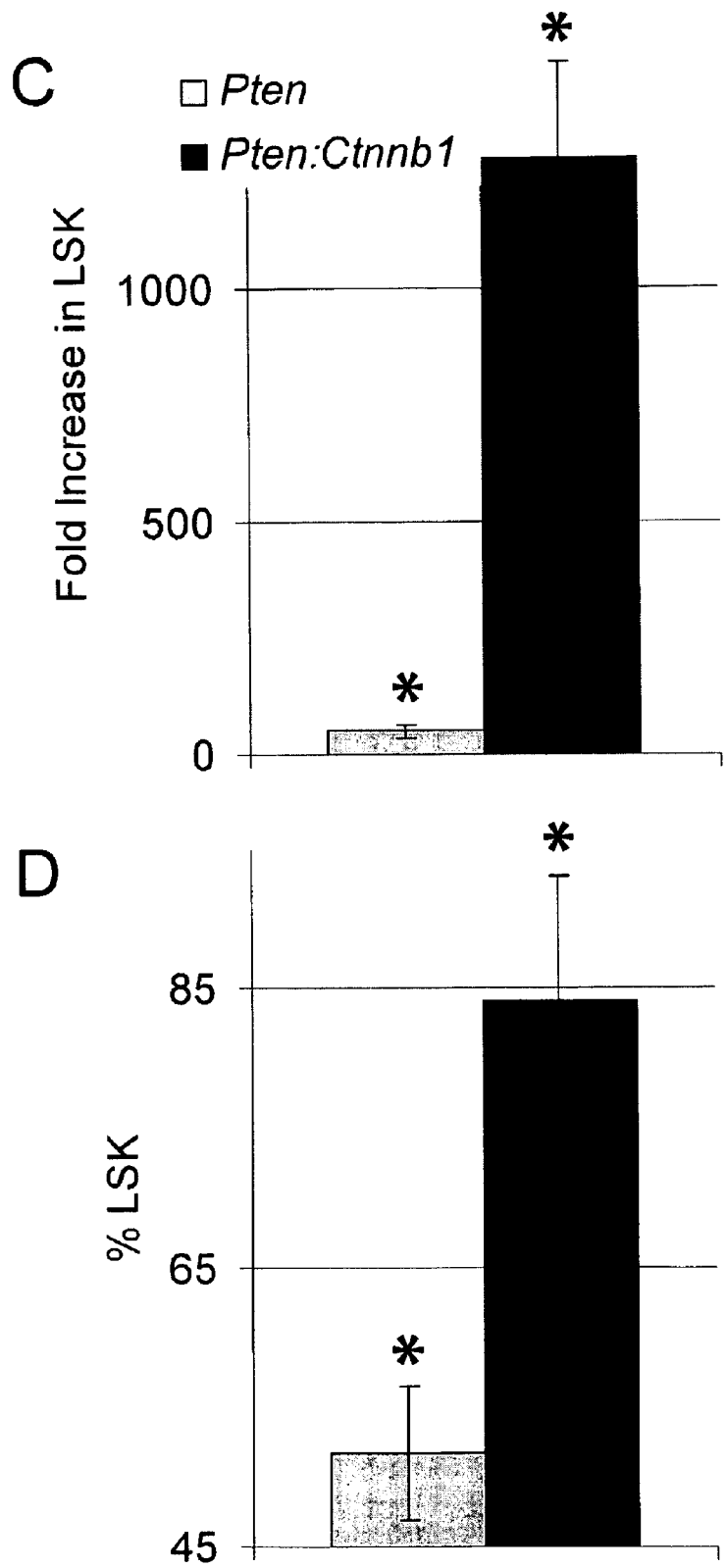
Figure 2:
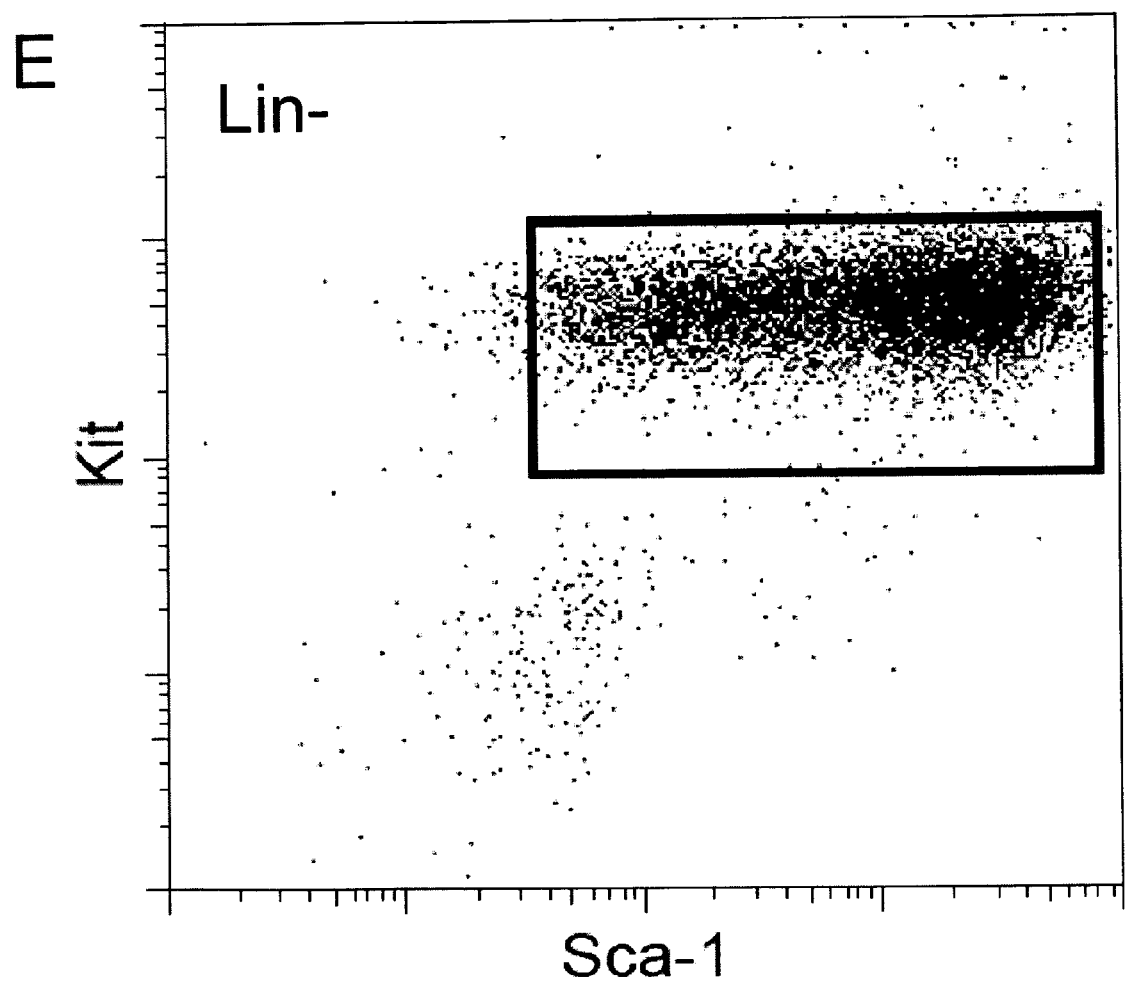
Figure 2:
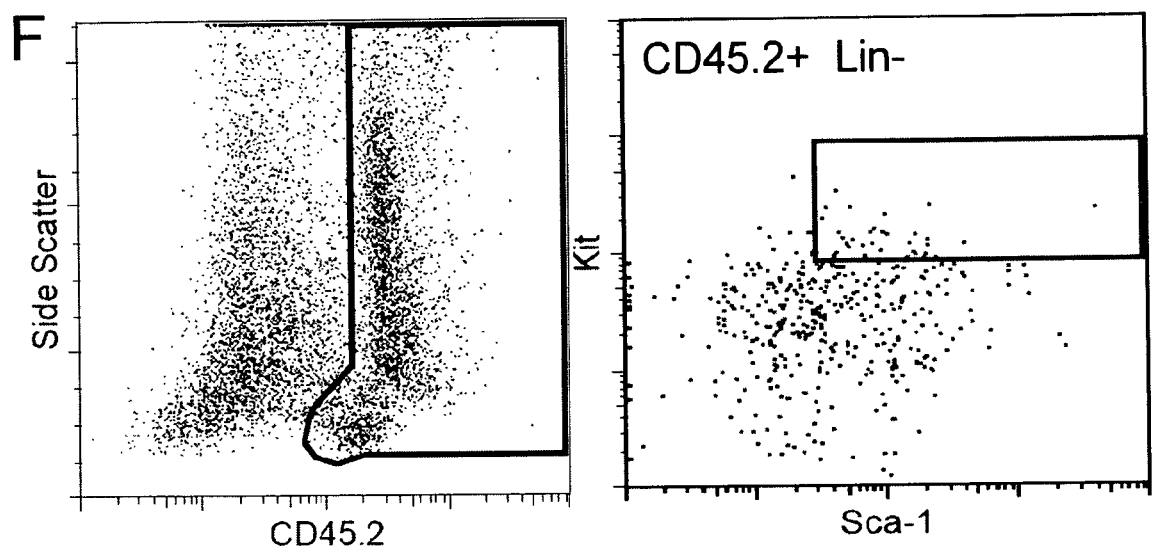
Figure 2:
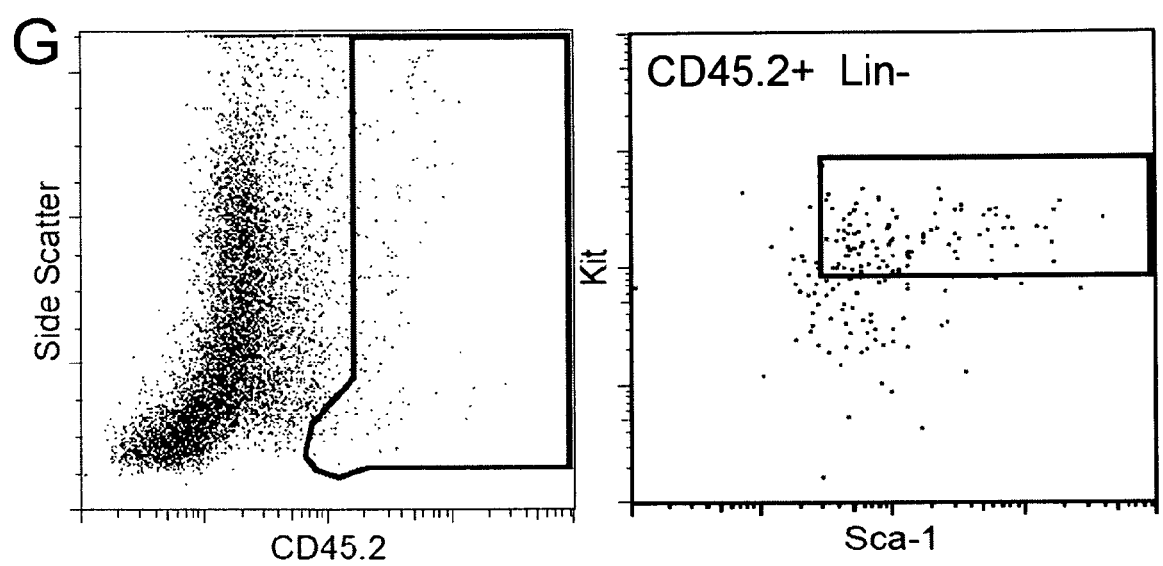
Figure 2:
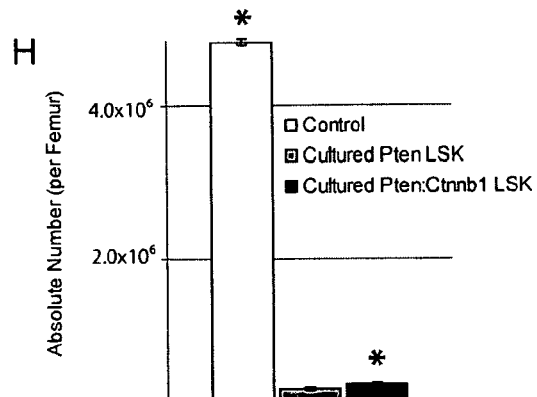
Figure 2:
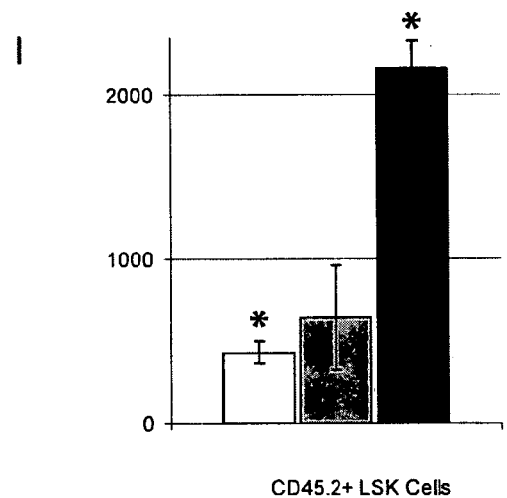
Figure 2:
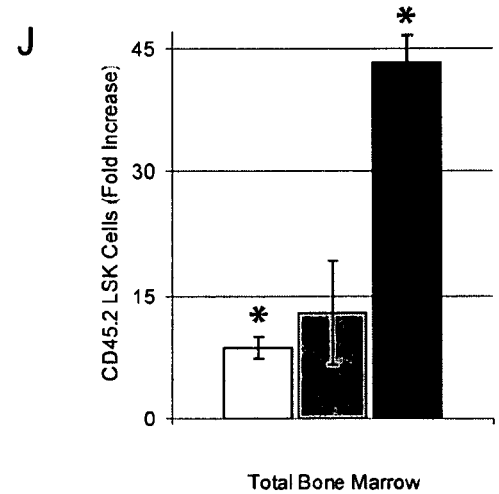

Collectively, these data demonstrate that the PTEN/Akt and Wnt/β-catenin signaling pathways can be manipulated pharmacologically to drive HSC expansion. The greatest expansion is achieved only by manipulating both pathways simultaneously. Functional, short-term HSCs show highest reconstitution ability when cultured in the presence of both inhibitors. Substantial longer-term reconstitution (8 weeks) occurs only when HSCs are cultured in the presence of both inhibitors but not when cultured with either single inhibitor or in the absence of either inhibitor. Thus, the pharmacological manipulation of both pathways simultaneously results in the greatest expansion of functional HSCs. This effect is reversible because recipient animals did not develop leukemia as genetic mutants did (FIG. 1) and cultured HSCs were able to differentiate unlike cultured HSCs from genetic mutants (FIG. 2).

Example 6

Culturing of HSC in Media Containing Biologics

Anti-GSK-3β and anti-PTEN antibodies may be made in accordance with procedures known in the art (or purchased, e.g., from Sigma, ExactAntigene, and Biocompare).

One hundred LSK Flk2⁻ cells are sorted from wild-type (C57Bl/6) mice and are cultured in (1) media, (2) media+an GSK-3β antibody, (3) media+an anti-PTEN antibody, and (4) media+anti-GSK-3β and anti-PTEN antibodies. Cells are cultured as described above. Cells are examined at 9 days, 17 days and 23 days of culture. The greatest expansion of HSCs is expected to occur when both antibodies are present.

Example 7

Culturing of HSC in Media Containing siRNA or RNAi

PTEN siRNA and GSK-3b siRNA may be made in accordance with procedures known in the art. (See, e.g., Mise-Omata S et al. *Biochem Biophys Res Commun.* 328 (4):1034-42 2005, or may be purchased from Biocompare).

One hundred LSK Flk2⁻ cells are sorted from wild-type (C57Bl/6) mice and are cultured in (1) media, (2) media+GSK-3β siRNA, (3) media+PTEN siRNA, and (4) media+GSK-3β siRNA and PTEN siRNA. Cells are cultured as described above. Cells are examined at 9 days, 17 days and 23 days of culture. The greatest expansion of HSC is expected to occur when both siRNAs are present.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for ex vivo expansion of a population of hematopoietic stem cells obtained from a tissue selected from the group consisting of peripheral blood, cord blood, and bone marrow, the method comprising inhibiting PTEN and GSK-3β in the population of stem cells to expand the number of stem cells.

2. The method according to claim 1, wherein:
(a) inhibiting PTEN comprises contacting the hematopoietic stem cell with an inhibitor of PTEN selected from the group consisting of a small molecule, a biologic, an antisense RNA, a small interfering RNA (siRNA), and combinations thereof; and
(b) inhibiting GSK-3β comprises contacting the hematopoietic stem cell with an inhibitor of a molecule in the Wnt pathway selected from a group consisting of a small molecule, a biologic, an antisense RNA, a small interfering RNA (siRNA), and combinations thereof.

3. The method according to claim 2, wherein inhibiting PTEN and inhibiting GSK-3β comprises contacting the stem cells with a small molecule inhibitor of PTEN and a small molecule inhibitor of GSK-3β.

4. The method according to claim 3, wherein the small molecule inhibitor of PTEN and the small molecule inhibitor of GSK-3β are reversible inhibitors.

5. The method according to claim 4, wherein the reversible PTEN inhibitor is selected from the group consisting of shikonin, a bisperoxovanadium compound, SF-1751 (Semafore Pharmaceuticals), pharmaceutical salts thereof, and combinations thereof.

6. The method according to claim 5, wherein the bisperoxovanadium compound is selected from the group consisting of bpV(phen)2, bpV(pic), pharmaceutical salts thereof, and combinations thereof.

7. The method according to claim 4, wherein the reversible GSK-3β inhibitor is selected from the group consisting of Hymenialdisine, Flavopiridol, Kenpaullone, Alsterpaullone, Azakenpaullone, Indirubin-30-oxime, 6-Bromoindirubin-30-oxime (BIO), 6-Bromoindirubin-30-acetoxime, Aloisine A, Aloisine B, TDZD8, Compound 12, CHIR98014, CHIR99021 (CT99021), CT20026, Compound 1, SU9516, ARA014418, Staurosporine, Compound 5a, Compound 29, Compound 46, GF109203x (bisindolylmaleimide I), Ro318220 (bisindolylmaleimide IX), SB216763, SB415286, I5, CGP60474, Compound 8b, TWS119, Compound 1A, Compound 17, Lithium, Beryllium, Zinc, small molecule GSK-3β inhibitors (Vertex Pharmaceuticals), NP-12 (Neuropharma), GSK-3β inhibitors (Amphora), GSK-3β inhibitors (CrystalGenomics), SAR-502250 (Sanofi-Aventis), 3544 (Hoffmann-La Roche), GSK-3β inhibitors (Lundbeck), TDZD-8 (Cancer Center, University of Rochester), pharmaceutically acceptable salts thereof, and combinations thereof.

8. The method according to claim 4, wherein the PTEN inhibitor is bpV(pic) and the GSK-3β inhibitor is CHIR99201.

9. The method according claim 1, wherein the expansion of the hematopoietic stem cells is by a factor of at least 40-fold.

10. The method according to claim 1, wherein the expansion of the number of stem cells is by a factor of at least 80-fold.

11. The method according to claim 1, wherein the expansion of the number of hematopoietic stem cells is by a factor of at least 150-fold.

12. The method according to claim 1, wherein the expansion of the number of hematopoietic stem cells is by a factor of at least 250-fold.

13. A method for ex vivo expansion of a hematopoietic stem cell population comprising inhibiting PTEN and GSK-3β in the hematopoietic stem cell population to expand the number of hematopoietic stem cells without significant differentiation of the hematopoietic stem cell population.

14. A method for ex vivo expansion of an hematopoietic stem cell (HSC) population obtained from a tissue selected from the group consisting of peripheral blood, cord blood, and bone marrow, the method comprising inhibiting PTEN and GSK-3β in the HSC population to expand the HSC population to a sufficient quantity while maintaining a multilineage differentiation potential in the HSC population, which is sufficient for subsequent transplantation into a patient in need thereof.

15. The method according to any one of claim 13 or 14, wherein:
(a) inhibiting PTEN comprises contacting the hematopoietic stem cell population with a PTEN inhibitor selected from the group consisting of a small molecule, a biologic, an antisense RNA, a small interfering RNA (siRNA), and combinations thereof; and
(b) inhibiting GSK-3β comprises contacting the hematopoietic stem cell population with a GSK-3β inhibitor selected from a group consisting of
a small molecule, a biologic, an antisense RNA, a small interfering RNA (siRNA), and combinations thereof.

16. The method according to claim 15, wherein inhibiting PTEN and GSK-3β comprises contacting the heatopoietic stem cell population with a small molecule inhibitor of PTEN and a small molecule inhibitor of GSK-3β .

17. The method according to claim 16, wherein the small molecule inhibitor of PTEN and the small molecule inhibitor of GSK-3β are reversible inhibitors.

18. The method according to claim 17, wherein the reversible PTEN inhibitor is selected from the group consisting of shikonin, a bisperoxovanadium compound, SF-1751 (Semafore Pharmaceuticals), pharmaceutical salts thereof, and combinations thereof.

19. The method according to claim 18, wherein the bisperoxovanadium compound is selected from the group consisting of bpV(phen)2, bpV(pic), pharmaceutical salts thereof, and combinations thereof.

20. The method according to claim 17, wherein the reversible GSK-3β inhibitor is selected from the group consisting of Hymenialdisine, Flavopiridol, Kenpaullone, Alsterpaullone, Azakenpaullone, Indirubin-30-oxime, 6-Bromoindirubin-30-oxime (BIO), 6-Bromoindirubin-30-acetoxime, Aloisine A, Aloisine B, TDZD8, Compound 12, CHIR98014, CHIR99021 (CT99021), CT20026, Compound 1, SU9516, ARA014418, Staurosporine, Compound 5a, Compound 29, Compound 46, GF109203x (bisindolylmaleimide I), Ro318220 (bisindolylmaleimide IX), SB216763, SB415286, 15, CGP60474, Compound 8b, TWS119, Compound 1A, Compound 17, Lithium, Beryllium, Zinc, small molecule GSK-3β inhibitors (Vertex Pharmaceuticals), NP-12(Neuropharma), GSK-3β inhibitors (Amphora), GSK-3β inhibitors (CrystalGenomics), SAR-502250 (Sanofi-Aventis), 3544 (Hoffmann-La Roche), GSK-3β inhibitors (Lundbeck), TDZD-8 (Cancer Center, University of Rochester), pharmaceutically acceptable salts thereof, and combinations thereof.

21. The method according to claim 17, wherein the PTEN inhibitor is bpV(pic), and the GSK-3β inhibitor is CHIR99201.

22. The method according to claim 13, wherein the HSC is obtained from a mammalian tissue selected from the group consisting of cord blood, peripheral blood, and bone marrow.

23. The method according to claim 14, wherein the expansion of the number of hematopoietic stem cells is by a factor selected from the group consisting of at least 40-fold, at least 80-fold, at least 150-fold, and at least 250-fold.

24. A method for ex vivo expansion of hematopoietic stem cells (HSCs) by at least 40-fold, the expanded HSCs being competent to reconstitute an HSC lineage upon transplantation into a mammalian patient in need thereof, the method comprising culturing a population of HSCs in a suitable culture medium comprising a PTEN inhibitor and a GSK-3β inhibitor.

25. The method according to claim 24, wherein the HSCs are obtained from a mammalian tissue selected from the group consisting of cord blood, peripheral blood, and bone marrow.

26. The method according to claim 24, wherein the mammal is a human.

27. The method according to claim 24, wherein the PTEN inhibitor is bpV(pic), and the GSK-3β inhibitor is CHIR99201.

28. The method according to claim 24, wherein the culture media comprises from about 100 to about 1000 nM of the PTEN inhibitor.

29. The method according to claims 24, wherein the culture media comprises from about 50 nM to about 500 nM of the GSK-3β inhibitor.

30. The method according to claim 24, wherein the expansion of the number of HSCs is by a factor selected from the group consisting of at least 80-fold, at least 150-fold, and at least 250-fold.

* * * * *